United States Patent [19]

Ochiai et al.

[11] 4,203,899
[45] May 20, 1980

[54] THIAZOLYLACETAMIDO COMPOUNDS

[75] Inventors: Michihiko Ochiai, Suita; Taiiti Okada, Kyoto; Osami Aki, Kawanishi; Akira Morimoto, Ikeda; Kenji Kawakita, Suita; Yoshihiro Matsushita, Nishinomiya, all of Japan

[73] Assignee: Takeda Chemical Industries, Ltd., Osaka, Japan

[21] Appl. No.: 897,239

[22] Filed: Apr. 17, 1978

Related U.S. Application Data

[62] Division of Ser. No. 642,356, Dec. 19, 1975, Pat. No. 4,098,888.

[51] Int. Cl.$^2$ .................. A61K 31/545; C07D 277/44
[52] U.S. Cl. ..................................... 548/194; 544/21; 544/22; 544/27; 424/246; 548/187; 548/195
[58] Field of Search ...................... 260/302 R, 306.8 R

[56] References Cited

U.S. PATENT DOCUMENTS

| | | | |
|---|---|---|---|
| 3,234,218 | 2/1966 | Schmidt et al. | 260/302 R |
| 3,631,055 | 12/1971 | Posselt et al. | 260/302 R |
| 3,755,347 | 8/1973 | Guillot et al. | 260/306.8 R |
| 3,948,925 | 4/1976 | Perronnet et al. | 260/302 R |
| 4,008,246 | 2/1977 | Ochiai et al. | 260/306.8 R |

OTHER PUBLICATIONS

Garraway, "Chemical Abstracts," vol. 74, 1971, Col. 75415a.

Primary Examiner—Donald G. Daus
Assistant Examiner—James H. Turnipseed
Attorney, Agent, or Firm—Wenderoth, Lind & Ponack

[57] ABSTRACT

Novel cephem compounds of the formula;

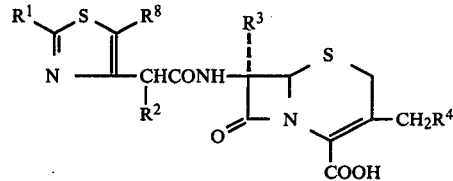

wherein $R^1$ represents amino or hydroxyl group which may be protected, $R^2$ represents amino or hydroxyl group or a group convertible into these groups, $R^3$ represents hydrogen or methoxy group or a group convertible into methoxy group, $R^4$ represents hydrogen or a residue of a nucleophilic compound and $R^8$ represents hydrogen or a halogen, or a pharmaceutically acceptable salt or ester thereof, have strong antibiotic properties against a wide variety of microorganisms including gram-positive bacteria as well as gram-negative ones, especially by oral administration and can be used as therapeutic agent for various bacterial infections of animals including human beings.

Also disclosed are novel thiazolylacetic acid compounds of the formula:

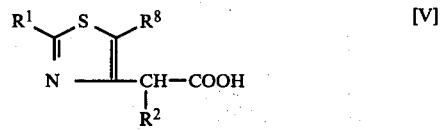

[V]

wherein $R^1$ represents amino, protected amino, hydroxyl or protected hydroxyl, $R^2$ represents amino, protected amino, hydroxyl, protected hydroxyl or the group

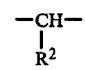

represents a group of the formula

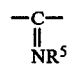

wherein $R^5$ represents hydroxyl or lower alkoxy and $R^8$ represents hydrogen or a halogen, or a salt, an ester or a reactive derivative thereof, and to processed for preparing these compounds. These latter compounds are useful as intermediates in the preparation of the novel cephem compounds.

12 Claims, No Drawings

THIAZOLYLACETAMIDO COMPOUNDS

This application is a divisional application of application Ser. No. 642,356, filed Dec. 19, 1975 now U.S. Pat. No. 4,098,888.

The present invention relates to cephem compounds of the formula:

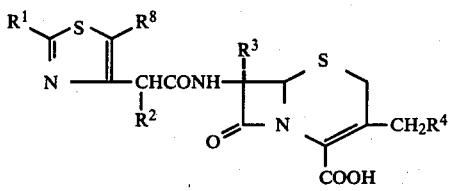 (I)

wherein $R^1$ represents amino or hydroxyl group which may be protected, $R^2$ represents amino or hydroxyl group or a group convertible into these groups, $R^3$ represents hydrogen or methoxy group or a group convertible into methoxy group, $R^4$ represents hydrogen or a residue of a nucleophilic compound and $R^8$ represents hydrogen or a halogen, or a pharmaceutically acceptable salt or ester thereof, intermediary compounds therefor, and to processes for preparing these compounds.

The present inventors, after extensive research, succeeded in synthesizing novel cephem compounds (I), by reacting a compound of the formula;

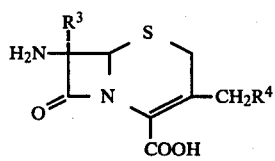 (VI)

wherein $R^3$ and $R^4$ are as defined above or a salt or ester thereof, with a compound of the formula;

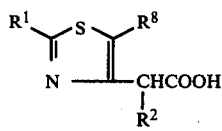 (V)

wherein $R^1$, $R^2$ and $R^8$ are as defined above or a reactive derivative thereof, or reducing a compound of the formula;

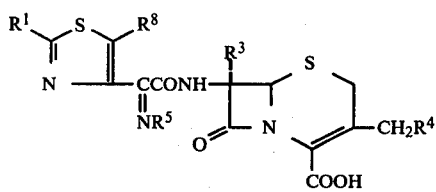 (VII)

wherein $R^5$ represents hydroxyl group which may be protected and each of other symbols has the same meaning as defined above or a salt or ester thereof, or reacting a compound of the formula;

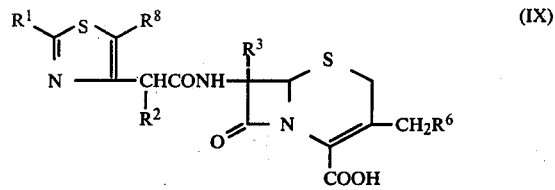 (IX)

wherein $R^6$ represents an acyloxy, carbamoyloxy group or a halogen and each of other symbols has the same meaning as defined above or a salt or ester thereof, with a nucleophilic compound, and found that the cephem compounds (I) obtained by the foregoing method have strong antibiotic properties against a wide variety of microorganisms including gram-positive bacteria as well as gram-negative ones, especially by oral administration and that the cephem compounds (I) can be used as therapeutic agent for various bacterial infections of animals including human beings.

The present invention is therefore directed to:
(1) A cephem compound (I),
A intermediary compound [V] for the cephem compound [I],
(3) A process for preparing a cephem compound [I], which comprises reacting a compound [VI] or a salt or ester thereof with a compound [V] or a reactive derivative thereof,
(4) A process for preparing a cephem compound [I], which comprises reducing a compound [VII] or a salt thereof,
(5) A process for preparing a cephem compound [I], which comprises reacting a compound [IX] or a salt thereof with a nucleophilic compound,
(6) A process for preparing a compound of the formula;

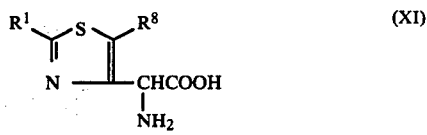 (XI)

wherein the symbols have the same meanings as defined above, or a salt or ester thereof, which comprises reducing a compound of the formula;

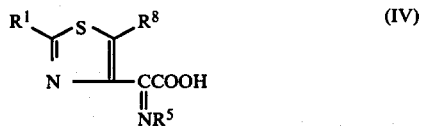 (IV)

wherein $R^5$ represents hydroxyl group which may be protected and each of other symbols has the same meaning as defined above, or a salt or ester thereof, followed by, if necessary, removal of the protective group.
(7) A process for preparing a compound of the formula;

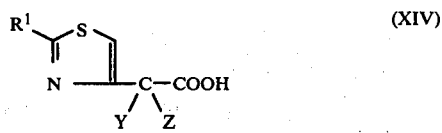 (XIV)

wherein R¹ represents amino or hydroxyl which may be protected and other symbols have the same meanings as defined below or a salt or ester thereof, which comprises reacting a compound of the formula;

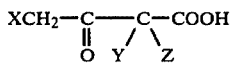 (XII)

wherein X means a halogen and, when Y is hydrogen, Z means amino group which may be protected or Y and Z together represent a group of the formula;

(R⁵ is hydroxyl group which may be protected) or a salt or ester thereof and a compound of the formula;

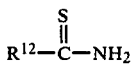 (XIII)

wherein R¹² represents a lower alkoxy group or amino group which may be protected, followed by, if necessary, removal of the protective group, (8) A process for preparing a compound of the formula;

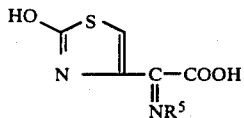 (XVI)

wherein the symbol has the same meaning as defined above or a salt or ester thereof, which comprises reacting a compound of the formula;

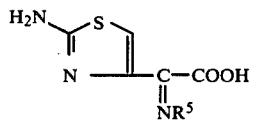 (XV)

wherein the symbol has the same meaning as defined above or a salt or ester thereof, with a diazotizing reagent, (9) A process for preparing a compound of the formula;

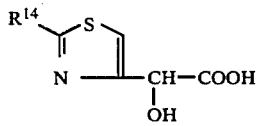 (XIX)

wherein the symbol has the same meaning as defined below or a salt or ester thereof, which comprises reacting a compound of the formula;

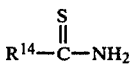 (XVII)

wherein R¹⁴ represents amino group which may be protected, withh trihalogenoacetone in the presence of a base to obtain a compound of the formula;

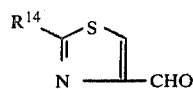 (XVIII)

wherein the symbol has the same meaning as defined above, subjecting the compound [XVIII] to addition reaction of hydrogen cyanide and hydrolyzing thus obtained product, followed by, if necessary, removal of the protective group, (10) A pharmaceutical composition containing compound [I].

In the cephem compounds [I], the symbol R¹ represents amino or hydroxyl group, or protected amino or hydroxyl group. The protected amino group means an amino group protected with such easily removable protective groups of amino group as usually employed in the peptide chemistry, which are exemplified by an alkylcarbonyl group such as formyl, acetyl, propionyl, etc., an alkoxycarbonyl group such as t-butoxycarbonyl, etc., an alkoxyalkylcarbonyl group such as methoxyacetyl, methoxypropionyl, etc., a substituted alkoxycarbonyl group such as trichloroethoxycarbonyl, etc., a substituted alkylcarbonyl such as monochloromethylcarbonyl, monochloroethylcarbonyl, dichloromethylcarbonyl, dichloroethylcarbonyl, trichloromethylcarbonyl, trichloroethylcarbonyl, trichloropropylcarbonyl, etc., an aralkyloxycarbonyl group such as benzyloxycarbonyl, etc., a substituted aralkyloxycarbonyl group such as p-nitrobenzyloxycarbonyl, etc. or amino group protected with proton. The protected hydroxyl group means a hydroxyl group protected with easily removable protective group of hydroxyl group. Such easily removable protective group of hydroxyl group may be exemplified by e.g. an acyl group such as formyl, acetyl, chloroacetyl, trifluoroacetyl, methoxyacetyl, phenoxyacetyl, benzoyl, benzoylformyl, p-nitrobenzoyl, ethoxycarbonyl, $\beta,\beta,\beta$-trichloroethoxycarbonyl, $\beta,\beta,\beta$-tribromoethoxycarbonyl, p-nitrophenoxycarbonyl, etc., an easily removable protective group under relatively mild conditions such as tetrahydropyranyl, tetrahydrothiofuranyl, methoxytetrahydropyranyl, etc. The symbol R² represents amino or hydroxyl group or a group convertible into these groups. The latter group includes those convertible into amino or hydroxyl group by e.g. reduction, oxidation, hydrolysis, etc. employing mild conditions which do not affect the cephem ring, as well the protected amino or hydroxyl groups mentioned above. As the group convertible into amino or hydroxyl group, the suitable examples are the same as that of the protective amino or hydroxyl group as mentioned in the symbol R¹, or a group of the formula;

wherein R⁵ is hydroxyl group which may be protected as exemplified below. In case of R² being a group of the formula; =NR⁵, the cephem compounds [I] may be shown by the formula;

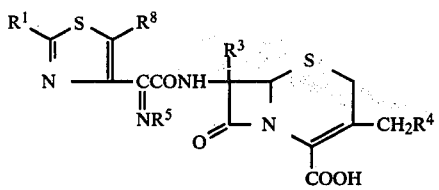

(VII)

wherein the symbols have the same meaning as defined above. The symbol R³ means hydrogen, methoxy group or a group convertible into methoxy group. As the group convertible into methoxy group, there may be employed such ones which are converted into methoxy group by the reaction with methanol as methylthio, methylseleno, etc. The symbol R⁸ represents hydrogen, or a halogen such as chlorine, bromide, etc. As the substituents at 3-position of the cephem compounds, there may be generally employed such ones as found in the corresponding moiety of cephalosporins produced by fermentation or as easily derivable therefrom. Therefore, the substituents may be exemplified by e.g. the formula: —CH₂R⁴. The residue of nucleophilic compound shown by the symbol R⁴ may be cyano, azido, amino, N-alkylamino (e.g. N-methylamino, N,N-dimethylamino, N-ethylamino, N,N-diethylamino, N-propylamino, etc.), hydroxyphenyl, a tertiary ammonium group or a group of the formula;

—W—R wherein W represents oxygen or sulfur atom and R represents hydrogen, carbamoyl, N-alkylcarbamoyl, thiocarbamoyl, N-alkylthiocarbamoyl, an acyl, sulfamoyl, alkylsulfonyl or heteror ring. The typical residue of mucleophilic compound may be exemplified by hydroxyl, mercapto, cyano, azido, amino, carbamoyloxy, carbamoylthio or thiocarbamoyloxy group, or those substituted with alkyl (e.g. methyl, ethyl, propyl, etc.), acyloxy (e.g. acetyloxy, propionyloxy, butyryloxy, benzoyloxy, p-chlorobenzoyloxy, p-methylbenzoyloxy, etc.), or a tertiary ammonium group, or hydroxyphenyl, sulfamoyloxy, an alkylsulfonyloxy, (cis-1,2-epoxypropyl)phosphono, etc. Furthermore, the symbol R⁴ may preferably represent a mercapto group substituted with a hetero ring which may be 5- or 6-membered one containing one to four hetero atoms selected from the group consisting of oxygen, sulfur and nitrogen. The hetero ring is exemplified by a 6-membered nitrogen-containing hetero ring e.g. pyridyl, N-oxido-pyridyl, pyrimidyl, pyridazinyl, N-oxido-pyridazinyl, etc. a 5-membered nitrogen-containing hetero ring e.g. pyrazolyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl, etc. and others. Each of these hetero ring may be further substituted and, as the substituents, there may be mentioned for example, lower alkyls such as methyl, ethyl, propyl, etc., lower alkoxyls such as methoxy, ethoxy, etc., halogens such as chlorine, bromine, etc., halogen substituted alkyls such as trifluoromethyl, trichloroethyl, etc., amino, mercapto, hydroxyl, carbamoyl, or carboxyl group, etc. The tertiary ammonium group represented by R⁴ may be exemplified by e.g. pyridinium, 3-methylpyridinium, 4-methylpyridinium, 3-chloropyridinium, 3-bromopyridinium, 3-iodopyridinium, 4-carbamoylpyridinium, 4-(N-hydroxymethylcarbamoyl)pyridinium, 4-(N-carbomethoxycarbamoyl)pyridinium, 4-(N-cyanocarbamoyl)pyridinium, 4-(carboxymethyl)pyridinium, 4-(hydroxymethyl)-6-pyridinium, 4-(trifluoromethyl)pyridinium, quinolinium, picolinium, lutidium, etc. Alternatively, 2-carboxyethenyl, chloro, methoxy group etc. may be substituted instead of the group represented by the formula; —CH₂R⁴. The sulfur atom in the cephem ring may be oxido-type. The carboxyl group at 4-position of the cephem ring may be free type, or salts with nontoxic cation such as sodium, potassium or the like; a basic amino acid such as arginine, ornithine, lysine, histidine or the like; or a polyhydroxyalkylamine such as N-methylglucamine, diethanolamine, triethanolamine, trishydroxymethylaminomethane or the like. Alterntively, the carboxyl group may be a biologically active ester derivative, said ester derivatives being conducive to, for instance, an increased blood level or/and a longer duration of activity. As the ester residues of use for this purpose, there may be mentioned, for example, alkoxymethyl and α-alkoxyethyl and other α-alkoxy-α-substituted methyl groups, e.g. methoxymethyl, ethoxymethyl, isopropoxymethyl, α-methoxyethyl, α-ethoxyethyl, etc.; alkylthiomethyl groups, e.g. methylthiomethyl, ethylthiomethyl, isopropylthiomethyl, etc.; and acyloxymethyl and α-acyloxy-α-substituted methyl groups, e.g. pivaloyloxymethyl, α-acetoxybutyl, etc.

Thus, the preferable examples of the present cephem compounds [I] may be the compounds that the group —CH₂R⁴ means methyl, acetoxymethyl, (1-methyl-tetrazol-5-yl)—thiomethyl, (1,2,3-triazol-5-yl)thiomethyl, (2-methyl-1,3,4—thiadiazol-5-yl)thiomethyl, etc. These compounds [I] are all novel and useful as antibiotics. Like the known cephalosporins or penicillins, the contemplated compounds [I] of this invention can each be administered in the forms of injection, capsules, tablets, granules, solutions, suspensions, solid forms, if necessary, with a physiologically acceptable carrier or excipient in accordance with the established pharmaceutical procedure. The contemplated compounds of this invention, such as sodium 7α-methoxy-7β-(2-aminothiazol-4-ylglycylamido)-3-(1-methyl-1H-tetrazol-5-ylthiomethyl)-3-cephem-4-carboxylic acid may be injected intramuscularly at a daily dose level of about 5 to 20 mg./kg. human body weight in 3 to 4 divided dose per day and are effective against respiratory-organ infections, urinary-tract infections, etc. And, the compounds [I] show strong antibiotic properties against a wide variety of microorganisms including gram-positive or negative bacteria, even by oral administration.

The cephem compounds [I] of the present invention can be prepared by e.g. the following processes:

(a) Reaction of compounds [V] and [VI].

The carboxyl group of the starting compounds [VI] of this reaction may be used as a salt form with alkali metals, organic amines such as sodium, potassium, triethylamine, etc., or as an ester form which can be easily converted into free carboxyl group by mild treatment with an acid or alkali, or by reduction, the ester being exemplified by e.g. with β-methylsulfonylethyl, trimethylsilyl, dimethylsilenyl, benzhydryl, β,β,β-trichloroethyl, phenacyl, p-methoxybenzyl, p-nitrobenzyl, methoxymethyl, etc. As the reactive derivatives of the other starting compounds [V], there may be employed acid halide, acid anhydride, mixed acid anhydride, cyclic carboxy-anhydride, active amide, ester, etc., thereof.

This reaction can be conducted advantageously and smoothly in the presence of a solvent. As said solvent, use may be made of the common solvents and their mixtures unless such solvents do not interfere with the present reaction. There may be mentioned, therefore, such solvents as water, acetone, tetrahydrofuran, dioxane, acetonitrile, chloroform, dichloromethane, dichloroethylene, dimethylformamide, dimethylacetamide, dimethylsulfoxide, etc. This reaction may proceed more advantageously when to the solvent there is added a base such as pyridine, triethylamine, N,N-dimethylaniline, sodium hydrogen carbonate, etc. The quantity of the base to be added is 100–300%, desirably 100–200% of that of the starting compounds [V]. While the reaction temperature is virtually optional, the reaction usually is carried out under cooling or at room temperature. The reaction is generally completed within several minutes to several hours.

If necessary, thus obtained compounds are subjected to removal of the protective group and/or conversion of the convertible group. The removal of the protective group of amino group may be conducted, for example, by acid treatment for t-butoxycarbonyl, etc., by a treatment with zinc and an acid for $\beta,\beta,\beta$-trichloroethoxycarbonyl, etc. by catalytic reduction for p-nitrobenzyloxycarbonyl, etc. The protective groups of hydroxyl group are removed, for example, by potassium hydrogen carbonate in aqueous methanol for formyl or trifluoroacetyl, etc., by diluted hydrochloric acid treatment, for tetrahydropyranyl, etc., by zinc and an acid treatment for $\beta,\beta,\beta$-trichloroethoxycarbonyl, etc. The ester residues of the carboxylic acids are removed, for example, by acid treatment for benzhydryl, p-methoxybenzyl, etc., by alkali treatment for $\beta$-methylsulfonylethyl, etc., by aqueous treatment for trimethylsilyl, dimethylsilenyl, etc., by zincan acid treatment for $\beta,\beta,\beta$-trichloroethyl, etc., by reduction for p-nitrobenzyl, etc. The methylthio or methylseleno group etc. may be converted into methoxy group by e.g. reacting methanol in the presence of metal compounds including silver, mercury, lead, thallium, etc. The removal of the protective groups or the conversion of the groups may be performed at the same time if possible, or any of them may be removed or converted in accordance with the sort of the groups and/or the reaction condition of the next step.

While the starting carboxylic acids [V] may occur as D- and L-isomers with respect to the $\alpha$-carbon, whichever of these isomers, as well as their mixture, can be successfully employed for the purposes of this invention. It is known that generally, of cephalosporins or penicillins having a center of asymmetry at $\alpha$-position, D-isomers are more antibiotic than the L-isomers.

The compounds [V] employed as the starting materials in this reaction may be prepared by, e.g. the processes (6) to (9) mentioned above, and are used in that condition obtained by these processes or after removal of the protecting groups and/or conversion of the groups.

The similar conditions as above are applied also to the reaction between the compounds [VI] and the compounds [IV].

(b) Reduction of the compounds [VII]

In the starting compounds [VII], the symbols other than $R^5$ have the same meanings as defined above, and symbol $R^5$ means hydroxyl group which may be protected. As the protective groups of hydroxyl group, any of the conventional ones may be used so far as they do not disturb the reactions of this invention and there may be generally employed a lower alkyl group such as methyl, ethyl, etc., an aryl group such as phenyl, thienyl, etc., an acyl group such as acetyl, benzoyl, etc.

The reduction condition employed in the present reaction may be selected from the known reduction methods so far as the compounds [VII] can be reduced into the compounds [I], and preferable ones are the catalytic reduction employing catalysts such as Raney nickel, platinum oxide, palladium-carbon, ruthenium-carbon, rhodium-carbon, copper-chromium oxide, etc., reduction means employing nascent hydrogen obtained by the co-existence of metals such as sodium, sodium amalgam, aluminum amalgam etc. and water, alcohols, etc. reduction means employing metallic hydride complexes such as lithium aluminum hydride, diethyl aluminum hydride, sodium aluminum hydride, sodium borohydride, etc., reduction means treating with metals such as zinc, iron, etc. in solvents such as acetic anhydride, formic acid, or aqueous mixture thereof, etc., electroreduction, etc. The reaction conditions such as reaction temperature, pressure, sort of the solvents, reaction time, and others are selected suitably according to the sort of starting materials, reduction means, etc. After the reduction reaction, the reaction mixture may be, if necessary, subjected to removal reaction of the protective group directly or after separation of the objective compounds [I]. The removal of the protective group is conducted in accordance with the conventional removing methods employed for the removal of each protective group.

(c) Reaction of the compounds [IX] with a nucleophilic compounds.

In the compounds [IX], the symbol $R^6$ represents carbamoyloxy, an acyloxy such as acetyloxy, propionyloxy, 3-oxobutyryloxy, 3-carboxypropionyloxy, 2-carboxybenzoyloxy, 4-carboxybutyryloxy, mandelyloxy, 2-(carboethoxycarbamoyl)-benzoyloxy, 2-(carboethoxysulfamoyl)benzoyloxy, 3-ethoxy-carbamoylpropionyloxy, etc., a halogen such as bromine, chlorine, etc. and among them the acyloxy groups are generally employed. The nucleophilic compounds correspond to the compounds having the symbol $R^4$ of the compounds [I] mentioned above. Among the nucleophilic compounds, the mercapto compounds are reacted each in such forms as the free compound or a salt with an alkali metal such as sodium potassium or the like. This reaction is desirably conducted in a solvent. For example, use can be made of water, heavy water or organic solvents readily miscible with water and inert to the starting compounds, such as dimethylformamide, dimethylacetamide, dioxane, acetone, alcohol, acetonitrile, dimethylsulfoxide, tetrahydrofuran, etc. The reaction temperature and time depend, among other factors, upon the starting compounds, solvent, etc. to be employed but generally the reaction is carried out at a selected temperature within the range of 0° to 100° C. for a selected time of a few hours to several days. The reaction is desirably conducted in the neighborhood of neutrality or between pH 2 and 8 and, for better results, between pH 5 and 8. The reaction often proceeds more smoothly by the addition of a quaternary ammonium salt having surface active effect (e.g. trimethylbenzylammonium bromide, triethylbenzylammonium bromide, triethylbenzylammonium hydroxide, etc.) to the reaction system. To prevent oxidation of the mercapto compounds, it is advantageous to carry out the reaction in an inert gaseous atmosphere, e.g. nitrogen gas.

The cephem compounds [I] obtained by the processes illustrated hereinbefore, can be purified by such procedures as column chromatography, extraction, precipitation, recrystallization, etc. The compounds [I], if desired, are further converted to contemplated salt or ester, etc. by a per se known process.

When $R^2$ represents a group of the formula; $=NR^5$, the compound [IX] may be represented by the formula;

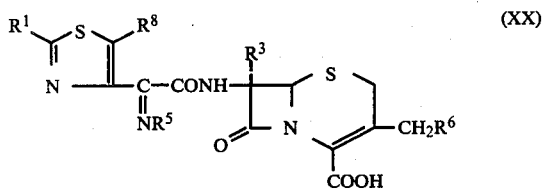

which may be reacted with nucleophilic compounds under a similar conditions mentioned above.

Each starting compound employed in the above mentioned processes for preparing the cephem compounds [I] can be prepared for example by the following processes.

(d) Reduction of the compounds [IV]

Similar reduction conditions as mentioned in above (b) are employed in this reaction. The carboxyl group of the starting compounds [IV] may be protected with a protective group removable under mild conditions which will not interfere with the thiazole ring, for example by acid or alkaline condition, reduction, etc. Therefore, such protective groups may be selected from those of carboxyl group generally employed in the peptide synthesis and are exemplified by alkali metals such as sodium, potassium, etc. alkyl such as methyl, ethyl, propyl, isopropyl, butyl, sec-butyl, isobutyl, tert-butyl, etc., substituted alkyl such as β-methylsulfonylethyl, trichloroethyl, diphenylmethyl, etc., aryl such as phenyl, tolyl, etc., substituted aryl such as p-tert-butylphenyl, p-nitrophenyl, etc., aralkyl such as benzyl, phenethyl, tolubenzyl, etc., substituted aralkyl such as p-methoxybenzyl, p-nitrobenzyl, etc. In the present reaction, it seems that the starting compound [IV] wherein $R^5$ is protected hydroxyl, gives better result. The contemplated compounds [V] may be purified by a per se known purification method such as solvent extraction, pH adjustment, crystallization, recrystallization, distillation, chromatography, ion-exchange chromatography, etc. The isolated compound [V] is DL-mixture and may be resolved into D-form and L-form respectively by introducing it to suitable optical-active-crystal-forming salt, e.g. salt with tartaric acid, mandelic acid, malic acid, camphor-sulfonic acid, etc.

(e) Reaction of the compounds [XII] with [XIII]

In the starting compounds [XII], the symbol X means halogen such as chlorine, bromine, iodine, fluorine, etc. When Y represents hydrogen, Z means amino group which may be protected, such group being exemplified above. Alternatively, Y and Z together represent a group of the formula; $=NR^5$, such group being also illustrated above. The carboxyl group of the compounds [XII] may be protected in a similar manner to that mentioned in respect of the compounds [IX]. In the present reaction, it is desirable to react substantially equivalent mole of both the starting compounds [XII] and [XIII]. The reaction is generally conducted in the solvent and such solvent may be selected from the organic solvent which will not disturb the contemplated reaction. Thus, methanol, ethanol, propanol, tetrahydrofuran, for example, are suitably employed. The reaction is carried out smoothly at room temperature or under reflux condition. The reaction is generally completed within one to several hours. The reaction may be carried out more smoothly by adding base such as dimethylaniline triethylamine, etc. to the reaction system. After the reaction is completed, the removal of the protecting group may be conducted directly to the reaction mixture or after isolation of the compounds [XIV], if desired. The purification of the compounds [XIV] may be carried out by the similar means as mentioned above (d). When the starting compounds [XIII] wherein $R^{12}$ represents a lower alkoxy group are employed, there is obtained a contemplated compound [XIV] wherein $R^1$ is hydroxyl according to the present reaction.

(f) Diazotization of the compounds [XV]

The carboxylic group of the starting compounds [XV] employed in this reaction may be protected by the similar manner as mentioned in the above compounds [IV]. The reaction is generally conducted in a solvent, for example, water or a mixture of water and organic solvents which are readily miscible with water and do not disturb the present reaction such as alcohols e.g. methanol, ethanol, etc., ethers e.g. tetrahydrofuran, dioxane, etc. As the diazotization reagents, nitrous acids, alkyl nitrites, nitrogen dioxide, nitrosyl chloride, etc. are conveniently employed and, among them, sodium nitrite, amyl nitrite, etc. are generally used. The reaction is generally conducted in the presence of an acid at a selected temperature within the range of 0° to 50° C. for a selected time of one to several hours. The acid employed in the reaction is exemplified by hydrochloric acid, sulfuric acid, phosphoric acid, formic acid, acetic acid, etc.

While α-oxyimino-2-substituted-thiazol-4-ylacetic acid derivatives involved in these compounds [XIV] and [XVI] may occur theoretically as syn- and anti-isomer with respect to oxyimino group, each of the both isomers can be used, similarly for the present reaction.

(g) Reaction of the compounds [XVII] and trihalogenoacetone

The symbol $R^{14}$ represents such amino group which may be protected as illustrated hereinbefore and, therefore, the compounds [XVII] are exemplified by N-(trichloroethoxycarbonyl)thiourea, N-(t-butoxycarbonyl)thiourea, N-(benzyloxycarbonyl)thiourea, etc. As the trihalogenoacetone, there are generally used, for example, 1,1,3-trichloroacetone, 1,1,3-tribromoacetone, etc.

The reaction may be carried out advantageously in the solvent. Any solvent which can dissolve both starting materials may be employed so far as it does not disturb the reaction, and more preferably one is exemplified by alcohols such as methanol, ethanol, propanol, etc., ketones such as acetone, methyl ethyl ketone, etc., ethers such as ether, tetrahydrofuran, dioxan, etc., or mixture thereof. The present reaction proceeds more smoothly in the presence of base such as pyridine, picoline, quinoline, isoquinoline, triethylamine, tributylamine, N-methylpiperidine, N-methylmorpholine, N,N-dimethylaniline, N,N-diethylaniline, etc. The reaction may proceed under room temperature and is accelerated by heating. Therefore, it is convenient to heat at about boiling point of the solvent employed. When a suitable conditions is selected in the present reaction, an intermediate i.e. 4-bromomethylthiazole may be obtained in some cases.

Thus obtained compounds [XVIII] are subjected to addition reaction of hydrogen cyanide to give so-called cyanhydrin compounds. For this purpose, cyanides such as sodium cyanide, potassium cyanide, etc. are generally reacted with the compounds [XVIII]. The cyanhydrin compounds can be isolated as stable acyl derivatives by protecting with a suitable protective group e.g. formyl, acetyl, etc. Example of the desirable procedure is to react acetic anhydride with the cyanhydrin compounds in pyridine. The reaction to obtain the cyanhydrin compounds or their derivatives is preferably conducted in the solvent in the presence of base. The solvent is desired to dissolve both of the starting compounds and base, and water or a mixture of water and organic solvent miscible with water (e.g. methanol, ethanol, acetone, dimethylformamide, etc.) are generally employed. As the base employed, there may be conveniently used, for example, such weak base as potassium dihydrogen phosphate, sodium hydrogen sulfite, triethylamine, etc. The reaction is carried out advantageously under cooling or at the neighborhood of room temperature to avoid undesirable side reaction. The reaction to obtain the cyanhydrin compounds as α-acetoxy-acetonitrile derivatives is usually conducted by reacting acetic anhydride with the former compounds in the solvent under the presence of base. In this reaction, any of solvent so far as it does not disturb the reaction may be employed and there may be generally used, for example, aprotic solvent such as chloroform, carbon tetrachloride, tetrahydrofuran, pyridine, dimethylformamide, etc., or mixture thereof. Any base so far as it does not disturb the present reaction can be employed and preferable ones are organic tertiary base such as pyridine, quinoline, isoquinoline, triethylamine, N,N-dimethylaniline, etc. Among them, pyridine is most preferable because it also works as solvent. Acetic anhydride mentioned above is most preferable as the acylating agent, but other acylating agent including acetyl chloride may be also employed. The reaction proceeds smoothly under cooling, but, if desired, it may be conducted in the neighborhood of room temperature.

Thus obtained cyanhydrin compounds containing their acyl derivatives are subjected to hydrolysis to give the contemplated compounds [XIX]. The hydrolysis is carried out in the solvent under the presence of acid or base. As the solvent, methanol or ethanol are generally used. The reaction is conducted advantageously under cooling to in the neighborhood of room temperature to avoid the undesirable side reaction. In the reaction, inorganic acid such as hydrochloric acid, sulfuric acid, etc. is preferably employed as acid and sodium hydroxide, potassium hydroxide, etc. is used as base.

While thus obtained α-hydroxyacetic acid derivatives [XIX] is racemic mixture, it can be resolved into optical active isomers i.e. D-form and L-form by per se known processes, for example, by introducing them into a suitable diasteromer.

The following are some examples of the preferable ones of the cephem compounds [I] of the present invention.

7β-[α-Hydroxy-α-(2-aminothiazol-4-yl)acetamido]-3-(1,2,3-triazol-5-ylthiomethyl)-3-cephem-4-carboxylic acid 7β-[(2-Aminothiazol-4-yl)glycylamido]-3-(1-methyl-1H-tetrazol-5-ylthiomethyl)-3-cephem-4-carboxylic acid 7β-[(2-Aminothiazol-4-yl)glycylamido]-3-(1,2,3-thiazol-5-ylthiomethyl)-3-cephem-4-carboxylic acid 7α-Methoxy-7β-[(2-aminothiazol-4-yl)glycylamido]-cephalosporanic acid 7α-Methoxy-7β-[(2-aminothiazol-4-yl)glycylamido]-desacetoxycephalosporanic acid 7β-[(2-Aminothiazol-4-yl)glycylamido]-3-(5-methyl-1,3,4-thiadiazol-2-ylthiomethyl)-3-cephem-4-carboxylic acid 7β-[α-Hydroxy-(2-aminothiazol-4-yl)acetamido]-3-(5-methyl-1,3,4-thiadiazol-2-ylthiomethyl)-3-cephem-4-carboxylic acid

EXAMPLE 1

A solution of 237 mg. of α-(β,β,β-trichloroethoxycarbonylamino)-α-[2-(β,β,β-trichloroethoxycarbonylamino)-thiazol-4-yl)acetic acid and 8 ml. of thionyl chloride is stirred at room temperature for 1.5 hours. The excess thionyl chloride is removed under reduced pressure. To the residue are added 183 mg. of 7-aminocephalosporanic acid and 5 ml. N,N-dimethylacetamide. The mixture is stirred for 4 hours and then 50 ml. of ethyl acetate and saturated aq. NaCl solution are added. The ethylacetate layer is separated and dried over magnesium sulfate, followed by the filtration. The filtrate is concentrated under reduced pressure to give 340 mg. of an oily residue. The residue is dissolved in excess 5% sodium hydrogen carbonate aq. solution and subjected to column chromatography on polystyrene resin (Registered trade mark, Amberlite XAD-2; manufactured by Rohm & Haas Co., U.S.A.), followed by elution with water. The combined eluate is concentrated to obtain sodium 7β-{α-(β,β,β-trichloroethoxycarbonylamino)-α-[2-(β,β,β-trichloroethoxycarbonylamino)thiazol-4-yl]-acetamido}cephalosporanate.

Analysis.-Calcd. for $C_{21}H_{19}N_5O_{10}S_2Cl_6Na.\frac{1}{2}H_2O$: C, 31.12; H, 2.48, Found: C, 30.96; H, 2.19.

NMR (ppm, 100 MHz, $CF_3CO_2D$): 2.25(3H,s,$CH_3CO$), 3.70(2H,q, 2-$CH_2$), 5.00(2H,s,$Cl_3CCH_2$), 8.12(1H,s,thiazole ring proton).

EXAMPLE 2

To a solution of 590 mg. of 7β-{-α-ethoxyimino-α-[2-(β,β,β-trichloroethoxycarbonylamino)thiazol-4-yl)acetamido}cephalosporanic acid in 30 ml. of 90% aq. formic acid is gradually added 654 mg. of zinc dust under stirring at 0° C. and the mixture is stirred for 1.5 hours at 0° C. The insoluble materials are filtered off and washed with 50% aq. formic acid. The filtrate and washings are concentrated under reduced pressure. The residue is dissolved in 20 ml. of water and hydrogen sulfide gas is bubbled through the solution for 20 minutes and insoluble material is filtered off. The filtrate is lyophilized to afford 380 mg. of the crude product, which is dissolved in 5% sodium hyrogen carbonate aq. solution and purified with a column packed with Amberlite XAD-2 (manufactured by Rohm & Haas Co., U.S.A.) to obtain sodium 7β-(2-aminothiazol-4-ylglycylamido)cephalosporanate.

Analysis - Calcd. for $C_{15}H_{16}N_5O_6S_2Na.3H_2O$: C, 35.78; H, 4.40; N, 13.90. Found: C, 35.22; H, 4.03; N, 13.74.

NMR (ppm, 100 MHz, $D_2O$): 2.25(3H,s,$CH_3CO$), 3.66(2H,q,2-$CH_2$), 5.26(1H,d,6-H), 5.30(1H,s,CH), 5.75(1H,d,7-H), 6.88 (1H,s,thiazole ring proton).

EXAMPLE 3

A solution of 1.40 g. of α-(β,β,β-trichloroethoxycarbonylamino)-α-[2-(β,β,β-trichloroethoxycarbonylamino)-thiazol-4-yl)acetic acid and 25 ml. of thionyl chloride is stirred at room temperature for 2 hours. The excess thionyl chloride is removed under reduced pessure. To the residue are added 1.10 g. of 7-aminocephalosporanic acid and 25 ml. of N,N-dimethylacetamide and the mixture is stired for 5 hours at room temperature. To the reaction mixture are added 250 ml. of ethyl acetate and saturated aq. NaCl solution. The ethyl acetate layer is separated, washed with water and dried over magnesium sulfate. The solvent is distilled off under reduced pressure and the oily residue is dissolved in 100 ml. of 90% formic acid. The solution is cooled to 0° C., followed by gradual addition of 5.0 g. of zinc dust and stirring for 3 hours at 0° C. The insoluble materials are filtered off and the filtrate is concentrated under reduced pressure. To the residue is added 30 ml. of water and hydrogen sulfide gas is passed through the aqueous solution for five minutes. The resulted insoluble materials are filtered off and the filtrate is concentrated under reduced pressure. The residue is dissolved in 5% sodium hydrogen carbonate aq. solution and purified with a column packed with polystyrene resin (Amberlite XAD-2; manufactured by Rohm & Haas Co., USA) in the same manner described in Example 1, to obtain sodium 7β-(2-aminothiazol-4-ylglycylamido)-cephalosporanate.

Analysis.-Calcd. for $C_{15}H_{16}N_5O_6S_2Na.2H_2O$: C, 37.11; H, 4.15. Found: C, 37.09; H, 3.93

EXAMPLE 4

To a solution of 4.0 g. of α-hydroxy-α-[2-(β,β,β-trichloroethoxycarbonylamino)thiazol-4-yl)acetic acid in 40 ml. of tetrahydrofuran is introduced phosgene gas for 10 minutes at 0° C. Excess phosgene is removed by bubbling nitrogen gas at 40° C. The solvent is removed under reduced pressure to give 4.6 g. of powdered cyclic carboxyanhydride.

Then 500 mg. of 7-aminocephalosporanic acid is suspended in 18 ml. of N,N-dimethylacetamide and 690 mg. of the cyclic carboxyanhydride is added under stirring. After stirring for 1 hour, 100 ml. of ethyl acetate is added and the ethyl acetate layer is separated, washed with water and extracted with 5% sodium hydrogen carbonate aq. solution. The extract is acidified to pH 2.0 with 1 N-hydrochloric acid. The acid solution is again extracted with ethyl acetate, and the ethyl acetate extract is washed with saturated aq. NaCl solution and dried over magnesium sulfate. The solvent is removed under reduced pressure to give 854 mg. of an oily residue, which is dissolved in 5% sodium hydrogen carbonate aq. solution and purified with a column packed with polystyrene resin (Registered trade mark, Amberlite XAD-2; manufactured by Rohm & Haas Co., USA) in the same manner described in Example 1, to obtain sodium 7β-{α-hydroxy-α-[2-(β,β,β-trichloroethoxycarbonylamino)-thiazol-4-yl]acetamido}cephalosporanate.

Analysis. - Calcd. for $C_{18}H_{16}N_4O_9S_2Cl_3Na.2\frac{1}{2}H_2O$: C, 32.22; H, 3.16; N, 8.35. Found: C, 32.16; H, 3.06; N, 7.84.

NMR(ppm, 100 MHz, $CF_3CO_2D$): 2.24(3H,s,$CH_3CO$), 3.70(2H,q, 2-$CH_2$), 4.98(2H,s,$Cl_3CCH_2$), 5.22(2H,q,3-$CH_2$), 5.28 (1H,d,6-H), 5.88(1H,d,7-H), 5.72(1H,s,CH), 7.48(1H, s,thiazole ring proton).

EXAMPLE 5

To a solution of 745 mg. of 7β-{α-hydroxy-α-[2-(β,β,β-trichloroethoxycarbonylamino)thiazol-4-yl)acetamido}cephalosporanic acid in 30 ml. of 90% formic acid is gradually added 800 mg. of zinc dust with stirring at 0° C. and the mixture is stirred for 2 hours at 0° C. The insoluble materials are filtered off and washed with 10 ml. of 50% formic acid. The filtrate and washings are concentrated under reduced pessure. The residue is dissolved in 5% sodium hydrogen carbonate aq. solution and the insoluble materials are filtered off. The filtrate is purified with a column packed with polystyrene resin (Amberlite XAD-2; manufactured by Rohm & Haas Co., USA) to obtain sodium 7β-[α-hydroxy-α-(2-aminothiazol-4-yl)acetamido]cephalosporanate.

Analysis. Calcd. for $C_{15}H_{15}N_4O_7S_2Na.2H_2O$: C, 37.04; H, 3.94; N, 11.52. Found: C, 36.70; H, 3.66; N, 11.86.

NMR (ppm, 100 MHz, $CF_3CO_2D$): 2.24(3H,s,$CH_3CO$), 3.70(2H,q, 2-$CH_2$), 5.23(2H,q,3-$CH_2$), 5.32(1H,d,6-H), 5.85(1H,d, 7-H), 5.56(1H,s,CH), 6.92(1H,s,thiazole ring proton).

EXAMPLE 6

To a suspension of 1.17 g. of α-ethoxyimino-α-[2-(β,β,β-trichloroethoxycarbonylamino)thiazol-4-yl]acetic acid in 20 ml. of water is added 3 ml. of 1 N-sodium hydroxide aq. solution. The resulted solution is lyophilized to give the sodium salt. To a suspension of the sodium salt in 30 ml. of benzene are added 889 mg. of oxalyl chloride and 1 drop of N,N-dimethylacetamide and the mixture is stirred for 1 hour at room temperature. The solvent is removed under reduced pressure and the residue is dissolved in 20 ml. of acetone.

The above solution of the acid chloride in acetone is dropwise added to a solution of 817 mg. of 7-aminocephalosporanic acid and 630 mg. of sodium hydrogen carbonate in 50 ml. of water and 25 ml. of acetone while stirring for 30 minutes at 0° C. The mixture is stirred for additional 2 hours at room temperature. Acetone is distilled off under reduced pressure and the aqueous layer is washed with ethyl acetate and acidified to pH 2.0 with 3 N-hydrochloric acid. The product is extracted with ethyl acetate and the combined extracts are washed with water and dried over anhydrous magnesium sulfate. Concentration of the extracts affords 970 mg. of an oily residue, 330 mg. of which is dissolved in 5% sodium hydrogen carbonate solution, subjected to column chromatography on polystyrene resin (Amberlite XAD-2; manufactured by Rohm & Haas Co., USA) and elution is carried out with 50% aqueous ethanol. The fractions containing the contemplated compound are pooled and lyophilized to obtain 184 mg. of sodium 7β-{α-ethoxyimino-α-[2-(β,β,β-trichloroethoxycarbonylamino)-thiazol-4-yl]acetamido}-cephalosporanate.

Analysis. - Calcd. for $C_{20}H_{19}N_5O_9S_2Cl_3Na.H_2O$: C, 35.07; H, 3.09; N, 10.23. Found: C, 35.24; H, 3.18; N, 10.33.

NMR(ppm, 100 MHz,$CF_3CO_2D$): 1.50(3H,t,$\underline{CH_3}CH_2$), 2.25(3H,s, $CH_3CO$), 3.37(2H,q,2-$CH_2$), 4.61(2H,q,$\underline{CH_2}CH_3$), 4.99 (2H,s,$Cl_3CCH_2$), 5.26(2H,q,$\overline{3-CH_2}$), 5.34(1H,d,6-H), 6.06(1H,d,7-H), 7.95(1H,s,thiazole ring proton).

EXAMPLE 7

To a suspension of 390 mg. of α-ethoxyimino-α-[2-(β,β,β-trichloroethoxycarbonylamino)thiazol-4-yl]a- cetic acid in 5 ml. of benzene are added 300 mg. of oxalylchloride and 1 drop of N,N-dimethylformamide and the mixture is stirred for 2 hours at room temperature. The solvent is removed under reduced pressure and the residue is dissolved in 10 ml. of acetone. The acetone solution is dropwise added while stirring for 30 minutes to a solution of 272 mg. of 7-aminocephalosporanic acid and 252 mg. of sodium hydrogen carbonate in 20 ml. of water and 10 ml. of acetone at 0° C. The mixture is stirred for additional 2 hours at room temperature and the solvent is distilled off under reduced pressure. The residual aqueous solution is washed with ethyl acetate and acidified to pH 2.0 with 1 N-hydrochloric acid. The solution is extracted with ethyl acetate and the combined extracts are washed with water and dried over anhydrous magnesium sulfate. Evaporation of the solvent affords 7β-{α-ethoxyimino-α-[2-(β,β,β-trichloroethoxycarbonylamino)thiazol-4-yl]-acetamido}-cephalosporanic acid. This product is identical with the compound obtained in Example 6 in NMR spectrum (in $CF_3CO_2D$).

EXAMPLE 8

To a suspension of 390 mg. of α-ethoxyimino-α-[2-(β,β,β-trichloroethoxycarbonylamino)thiazol-4-yl]acetic acid in 10 ml. of methylene chloride is added with stirring 312 mg. of phosphorus pentachloride.

The mixture becomes homogeneous while stirring within 10 seconds. After stirring for additional one hour at room temperature, the solvent is distilled off under reduced pressure and the residue is dissolved in 5 ml. of acetone. The acetone solution is dropwise added for 50 minutes to a solution of 272 mg. of 7-aminocephalosporanic acid and 840 mg. of sodium hydrogen carbonate in 10 ml. of water and 5 ml. of acetone at 0° C. The mixture is stirred for additional 2 hours at room temperature and acetone is removed under reduced pressure. The residual aqueous solution is washed with ethyl acetate and acidified to pH 2.0 with 1 N hydrochloric acid. The solution is extracted with ethyl acetate and the extracts are washed with water and dried over anhydrous magnesium sulfate. Removal of the solvent gives 7β-{α-ethoxyimino-α-[2-(β,β,β-trichloroethoxycarbonylamino)thiazol-4-yl]acetamido}cephalosporanic acid. This product is identical with the compound obtained in Example 6 in NMR spectrum (in $CF_3CO_2D$).

EXAMPLE 9

To a suspension of 347 mg. of α-oxyimino-α-[2-(β,β,β-trichloroethoxycarbonylamino)thiazol-4-yl]acetic acid in 20 ml. of water is added 2 ml. of 1 N-sodium hydroxide solution. The solution is lyophilized to give the sodium salt. To a suspension of the sodium salt in 10 ml. of benzene are added 300 mg. of oxalyl chloride and 1 drop of N,N-dimethylacetamide and the mixture is stirred for 1 hour at room temperature. The solvent is distilled off under reduced pressure and the residue is dissolved in 10 ml. of acetone. The acetone solution is dropwise added to a solution of 261 mg. of 7-amino-cephalosporanic acid and 200 mg. of sodium hydrogen carbonate in 10 ml. of water under stirring at 0° C. in the course of 10 minutes. The mixture is stirred for additional 2 hours at room temperature. Acetone is distilled off under reduced pressure and the aqueous solution is washed with ethyl acetate and acidified to pH 2.0 with 1 N-hydrochloric acid. The product is extracted with ethyl acetate and the combined extracts are washed with water and dried over anhydrous magnesium sulfate. Evaporation of the solvent affords 7β-{α-oxyimino-α-[2-(β,β,β-trichloroethoxycarbonylamino)thiazol-4-yl]acetamido}-cephalosporanic acid.

NMR (ppm, 100 MHz, $CDCl_3+d_6$-DMSO): 2.00(3H s,$CH_3CO$),3.46 (2H,q,2-$CH_2$), 4.85(2H,s,$Cl_3CCH_2$), 4.96(2H,q,3-$CH_2$), 5.06(1H,d,6-CH), 5.89(1H,q,7-CH), 7.39(1H s,thiazole ring proton), 9.26(1H,d,7-NH).

EXAMPLE 10

A solution of 900 mg. of α-(β,β,β-trichloroethoxycarbonylamino)-α-[2-(β,β,β-trichloroethoxycarbonylamino)-thiazol-4-yl]acetic acid and 15 ml. of thionyl chloride is stirred at room temperature for 1.5 hours. The excess thionyl chloride is removed under reduced pressure. To the oily residue are added 700 mg. of 7-aminocephalosporanic acid and 15 ml. of N,N-dimethylacetamide and the mixture is stirred for 4 hours at room temperature. The reaction mixture is added 100 ml. of ethyl acetate and then is washed with saturated aq. NaCl solution. The ethyl acetate layer is separated and dried over magnesium sulfate. The solvent is removed under reduced pressure to give an oily residue, which is dissolved in 50 ml. of 90% formic acid. The solution is cooled to 0° C. and 2.0 g. of zinc dust is gradually added. The mixture is stirred for 1.5 hours at 0° C. The insoluble materials are filtered off and the filtrate is concentrated under reduced pressure. To the residue is added 20 ml. of water and then hydrogen sulfide gas is passed through the aqueous solution. The resulted insoluble materials are filtered off and the filtrate is concentrated under reduced pressure. The residue is dissolved in 5% sodium hydroxide carbonate aq. solution and purified with a column packed with polystyrene resin (Amberlite XAD-2; manufactured by Rohm & Haas Co., USA) in the same manner described in Example 1, to obtain sodium 7β-(2-aminothiazol-4-ylglycylamido)-cephalosporanate. This product is identical with the compound obtained in Example 2 in all respects.

EXAMPLE 11

To a suspension of 1.563 g. of α-ethoxyimino-α-[2-(β,β,β-trichloroethoxycarbonylamino)thiazol-4-yl]acetic acid in 20 ml. of methylene chloride is added 1.250 g. of phosphorus pentachloride while stirring. The mixture is stirred for 1 hour at room temperature and concentrated under reduced pressure. The residue is dissolved in 20 ml. of acetone. The acetone solution thus obtained is dropwise added to a solution of 857 mg. of 7-amino desacetoxy cephalosporanic acid and 1.68 g. of sodium hydrogen carbonate in 40 ml. of water and 20 ml. of acetone at 0° C. under stirring in the course of 30 minutes. The mixture is stirred for 2 hours at room temperature and acetone is distilled off under reduced pressure. The residual aqueous solution is washed with ethyl acetate, acidified to pH 2.0 with 1 N-hydrochloric acid and extracted with ethyl acetate. The combined extracts are washed with water and dried over anhydrous magnesium sulfate. Evaporation of the solvent affords 2.04 g. 7β-{α-ethoxyimino-α-[2-(β,β,β-trichloroethoxycarbonylamino)thiazol-4-yl]acetamido}-desacetoxycephalosporanic acid. Yield 86.9%.

NMR (ppm, 100 MHz, $CDCl_3+d_6$-DMSO): 1.26(3H,t,$CH_3CH_2$), 2.13(3H,s,3-$CH_3$), 3.40(2H,q,2-$CH_2$), 4.23(2H,q,$\underline{CH_2}CH_3$), 4.86(2H,s,$ClCCH_2$), 5.06(1H,d, 6-H), 5.80(1H,q,7-H), 7.26 and 7.83(1H, two s, thiazole ring proton).

573 mg. of the acid obtained in the above method is dissolved in 5% sodium hydrogen carbonate aq. solution, subjected to column chromatography on polystyrene resin, Amberlite XAD-2 (manufactured by Rohm & Haas Co., USA) and eluted with 50% aqueous ethanol. The fractions containing the contemplated compound are pooled and lyphilized to obtain 233 mg. of sodium 7β-{α-ethoxyimino-α-[2-(β,β,β-trichloroethoxycarbonylamino)thiazol-4-yl]acetamido}desacetoxycephalosporanate. Yield 39.2%. Analysis-Calcd. for $C_{18}H_{17}N_5O_7S_2Cl_3Na.H_2O$: C, 34.49; H, 3.06; N, 11.17. Found: C, 34.96; H, 3.43; N, 11.17.

EXAMPLE 12

To a solution of 1.467 g. of 7β-{α-ethoxyimino-α-[2-(β,β,β-trichloroethoxycarbonylamino)thiazol-4-yl]-acetamido}-desacetoxycephalosporanic acid in 80 ml. of 90% aq. formic acid is gradually added 1.634 g. of zinc dust at 0° C. and the mixture is stirred for 1.5 hours at 0° C. The insoluble material is filtered off and washed with 50% aq. formic acid. The filtrate and washings are concentrated under reduced pressure and 200 ml. of water is added to the residue. Hydrogen sulfide gas is bubbled through the aqueous solution and insoluble material is filtered off. The filtrate is lyophilized to yield 1.15 g. of the formate. Yield 100%. The formate is dissolved in 5% sodium hydrogen carbonate aq. solution and purified with a column packed with Amberlite XAD-2 (manufactured by Rohm & Haas Co., USA) to afford 614 mg. of sodium 7β-(2-aminothiazol-4-ylglycylamido)desacetoxycephalosporanate. Yield 62.7%.

Analysis-Calcd. for $C_{13}H_{14}N_5O_4S_2Na.1\frac{1}{2}H_2O$: C, 37.31; H, 4.10; N, 16.74. Found: C, 37.81; H, 4.24; N, 16.69. NMR(ppm, 100 MHz, $D_2O$): 2.05(3H,s,3-$CH_3$), 3.48(2H,q,2-$CH_2$), 5.13(1H,s,CH), 5.18(1H,d,6-H), 5.79(1H,d,7-H), 6.99(1H,s,thiazole ring proton).

EXAMPLE 13

A mixture of 650 mg. of α-ethoxyimino-α-(2-hydroxythiazol-4-yl)acetic acid and 750 mg. of phosphorus pentachloride in 50 ml. of dry ether is stirred for 2 hours at room temperature. The acid chloride solution is added to a suspension of 1.10 g. of 7-aminocephalosporanic acid in 30 ml of N,N-dimethylacetamide and the mixture is stirred for 3.5 hours at room temperature. To the mixture is added 200 ml. of ethyl acetate and the organic solution is washed 7 times with water. The ethyl acetate layer is concentrated under reduced pressure and the residue is dissolved in 5% sodium hydrogen carbonate aq. solution and purified with a column packed with Amberlite XAD-2 to afford sodium 7β-(α-ethoxyimino-α-(2-hydroxythiazol-4-yl)acetamido)cephalosporanate.

Analysis-Calcd. for $C_{17}H_{17}N_4O_8S_2Na.3H_2O$: C, 37.36; H, 4.24; N, 10.25. Found: C, 37.37; H, 3.90; N, 9.86 NMR(ppm, 100 MHz, $CF_3CO_2D$): 1.44(3H,t,$CH_3CH_2$), 2.21(3H,s,$CH_3CO$), 3.70(2H,q,2-$CH_2$), 4.48(2H,q,$CH_2CH_3$), 5.25(2H,q,3-$CH_2$), 5.30(1H,d,6-H), 6.05(1H,$\overline{d}$,7-H), 7.13(1H,s,thiazole ring proton).

EXAMPLE 14

To a suspension of 1.08 g. of α-ethoxyimino-α-(2-hydoxythiazol-4-yl)acetic acid in 20 ml. of absolute ether is added 1.25 g. of phosphorus pentachloride and the mixture is stirred for 2 hours at room temperature.

The acid chloride solution is dropwise added to a suspension of 1.80 g. of 7-aminocephalosporanic acid in 50 ml. of N,N-dimethylacetamide and the mixture is stirred for 4 hours at room temperature. The mixture is extracted 3 times with each 120 ml. of ethyl acetate and the combined extracts are washed with water and dried over anhydrous magnesium sulfate. The solvent is removed and the residue is dissolved in 60 ml. of 90% aq. formic acid. To the acidic solution is added 4.30 g. of zinc dust at 0° C. and the mixture is stirred for 2 hours at this temperature.

Insoluble material is filtered off and the filtrate is concentrated under reduced pressure. To the residue is added 20 ml. of water and hydrogen sulfide gas is bubbled through the aqueous solution for 5 minutes. Insoluble material is filtered off and the filtrate is again concentrated. The residue is dissolved in 5% sodium hydrogen carbonate aq. solution and purified with a column packed with Amberlite XAD-2. The fractions obtained by the eluation with 5% aqueous ethanol is lyophilized to afford sodium 7β-(2-hydroxythiazol-4-ylglycylamido)-cephalosporanate.

Analysis-Calcd. for $C_{15}H_{15}N_4O_7S_2Na.H_2O$: C, 38.46; H, 3.66; N, 11.96. Found: C, 38.35; H, 4.04; N, 12.28.

EXAMPLE 15

A solution of 10.0 g. of N-(β,β,β-trichloroethoxycarbonyl)thiourea, 12.0 g. of 1,1,3-tribromoacetone and 5.0 g. of dimethylaniline in 100 ml. of ethanol is heated under reflux for 2 hours. After cooling, ethanol is removed under reduced pressure, and the oily residue is dissolved in ethyl acetate. Ethyl acetate layer is washed with water and dried over $MgSO_4$. Ethyl acetate is removed under reduced pressure and the oily residue is dissolved in small quantity of chloroform. From the solution which is allowed to stand at room temperature is obtained 2-(β,β,β-trichloroethoxycarbonyl)amino-4-formylthiazole as a crystalline form. 5.0 g. Melting point: 188°–190° C.

Analysis-Calcd. for $C_7H_5O_3N_2SCl_3$: C, 27.69; H, 1.66; N, 9.23. Found: C, 27.87; H, 1.69; N, 9.01.

NMR (ppm, 100 MHz, $CDCl_3$-$d_6$ DMSO); 5.05(2H,s,$Cl_3CCH_2$-), 8.05(1H,s,5-H), 9.80(1H,s,CHO)

EXAMPLE 16

To a mixture of 1.0 g. of 2-(β,β,β-trichloroethoxycarbonyl)amino-4-formylthiazole, 0.87 g. of $KH_2PO_4$, 6 ml. of water and 4 ml. of dimethylformamide is added 0.33 g. of KCN at room temperature and the mixture is stirred for 30 minutes. The reaction mixture is extracted with ethyl acetate and the ethyl acetate layer is washed with water and dried. Evaporation of ethyl acetate gives α-hydroxy-[2-(β,β,β-trichloroethoxycarbonyl)aminothiazol-4-yl]acetonitrile 1.127 g.

NMR (ppm, 100 MHz, $CDCl_3$): 4.90(2H,s,$Cl_3CCH_2$—), 5.70(1H,s,—CHCN), 7.90(1H,s,5H).

EXAMPLE 17

To a solution of 1.10 g. of α-hydroxy-[2-(β,β,β-trichloroethoxycarbonyl)aminothiazol-4-yl]acetonitrile in 1 ml. of pyridine is added 2.5 ml. of acetic anhydride under ice-cooling and the mixture is stirred for 1 hour. To the mixture is added ether and water and the organic layer is washed with aq. $NaHCO_3$ and further water in this order. Evaporation of ether gives α-acetoxy-[2-(β,β,β-trichloroethoxycarbonyl)aminothiazol-4-yl]acetonitrile. 1.3 g.

NMR(ppm, 100 MHz, CDCl$_3$): 2.20(3H,s,COCH$_3$), 5.00(2H,s,Cl$_3$CCH$_2$—), 6.60(1H,s,>CHCN), 7.30(1H,s,5-H).

EXAMPLE 18

To a solution of 1.30 g. of α-acetoxy-[2-(β,β,β-trichloroethoxycarbonyl)aminothiazol-4-yl]acetonitrile in 10 ml. of methanol is bubbled gaseous hydrochloric acid for 10 minutes under ice-cooling, and the mixture is kept standing at room temperature for 1 hour. After evaporation of methanol is added 40 ml. of 50% aq. methanol to the residue and stirred for 1 hour. To this reaction mixture is added 1.0 g. of NaOH and stirred for 1 hour. Methanol is removed under reduced pressure and the residue is extracted with ethyl acetate after being made acidic with N-HCl. Ethyl acetate layer is washed with water and dried. Ethyl acetate is removed under reduced pressure to obtain α-hydroxy-[2-(β,β,β-trichloroethoxycarbonyl)aminothiazol-4-yl]acetic acid. 0.996 g. Melting point: 135°–136° C.

Analysis-Calcd. for C$_8$H$_7$O$_5$N$_2$SCl$_3$: O, 27.48; H, 2.02; N, 8.01. Found: C, 27.72; H, 2.05; N, 8.08.

NMR(ppm, 100 MHz, CDCl$_3$): 4.90(2H,s,Cl$_3$CCH$_2$—), 5.40(1H,s,>C$\underline{H}$—COOH), 7.10(1H,s,5-H).

EXAMPLE 19

To a solution of 21.43 g. of ethyl α-ethoxyimino-β-oxo-γ-bromobutyrate in 80 ml. of ethanol is added 8.81 g. of methylthionocarbamate and the mixture is heated under reflux for 1.5 hours. After cooling ethanol is removed under reduced pressure and the oily residue is dissolved in chloroform. The chloroform solution is washed, dried, and condensed. The condensate is purified by silica gel chromatography to give 11.9 g. of ethyl α-ethoxyimino-(2-hydroxythiazol-4-yl)acetate. Melting point: 54°–55° C.

Analysis-Calcd. for C$_9$H$_{12}$O$_4$N$_2$S: C, 44.25; H, 4.95; N, 11.47. Found: C, 44.54; H, 5.04; N, 11.53.

NMR(ppm, 100 MHz, CDCl$_3$): 6.33(1H,s,5-H).

EXAMPLE 20

To a solution of 10 g. of ethyl α-ethoxyimino-(2-hydroxythiazol-4-yl)acetate in 30 ml. of ethanol is added a solution of 11.47 g. of KOH in 50 ml. of water at room temperature and the mixture is stirred for 25 minutes. The reaction mixture is condensed under reduced pressure and is made acidic with 10% aq. HCl. Ethyl acetate extract of the reaction mixture is extracted with 10% aq.NaHCO$_3$. The aqueous layer is then made acidic with 10% aq.HCl and extracted again with ethyl acetate. From the ethyl acetate extract, after being washed, dried and condensed is obtained a crystalline substance. Recrystallization from benzene-ethanol gives α-ethoxyimino-(2-hydroxythiazol-4-yl)acetic acid. 7.5 g. Melting point: 131.5° C. (dec.).

Analysis-Calcd. for C$_7$H$_8$O$_4$N$_2$S: C, 38.88; H, 3.72; N, 12.95. Found: C, 38.65; H, 3.85; N, 13.06.

NMR(ppm, 100 MHz, d$_6$-DMSO): 6.64(1H,s,5-H).

EXAMPLE 21

To a mixture of 1 g. of α-ethoxyimino-(2-hydroxythiazol-4-yl)acetic acid, 10 ml. of 50% aq. formic acid and 5 ml. of methanol is added gradually 0.9 g. of zinc dust under ice-cooling. The mixture is stirred for 1 hour at this state and then for 30 minutes at room temperature. The reaction mixture is filtered and the filtrate is passed through a column packed with ion-exchange resin (Amberlite IR-120(H)] to give purified 2-hydroxythiazol-4-ylglycine.

Analysis-Calcd. for C$_5$H$_6$O$_3$N$_2$S: N, 16.08. Found: N, 15.96

NMR(ppm, 100 MHz, CF$_3$COOD): 5.56(1H,s, >C$\underline{H}$—COOH), 6.91(1H,s,5-H).

EXAMPLE 22

To a mixture of 40 ml. of C.HCl and 100 ml. of water is dissolved under ice-cooling 8.8 g. of ethyl α-oxyimino-(2-aminothiazol-4-yl)acetate. A solution of 2.8 g. of NaNO$_2$ in 20 ml. of water is added dropwise to this solution in a period of 20 minutes. After being stirred for 2.5 hours under ice-cooling the reaction mixture is extracted with 200 ml. of ethyl acetate. The extract is washed with water and dehydrated. The ethyl acetate is distilled off and the resultant oil is purified by silica gel chromatography to give ethyl α-oxyimino-(2-hydroxythiazol-4-yl)-acetate.

NMR(ppm, 100 MHz, CDCl$_3$): 1.37(3H,t,CH$_2$C$\underline{H}_3$), 4.36(2H,q,C$\underline{H}_2$CH$_3$), 8.02(1H,s,5-H).

EXAMPLE 23

To a solution of 1.3 g. of ethyl α-oxyimino-(2-hydroxythiazol-4-yl)acetate in 5 ml. of ethanol is added under ice-cooling 30 ml. of 50% aq. formic acid. Zinc dust (1.17 g.) is added gradually to this solution in a period of 5 minutes under stirring. The reaction mixture is stirred for 2 hours under ice-cooling and filtered. The filtrate is condensed under reduced pressure and the residue is poured into 10 ml. of water. The water layer is neutralized with 10% aq. NaHCO$_3$ and then extracted with ethyl acetate. The extract is washed with water and dehydrated. The ethyl acetate is distilled off and the resultant oil is purified by silica gel chromatography to give ethyl 2-hydroxythiazol-4-ylglycine.

NMR (ppm, 100 MHz, CDCl$_3$): 1.22(3H,t,—CH$_2$C$\underline{H}_3$), 4.27(2H,q,—C$\underline{H}_2$CH$_3$), 4.65(1H,s, >C$\underline{H}$— COOC$_2$H$_5$), 7.14(1H,s,5-H).

The ester is acylated with β,β,β-trichloro ethyl chloroformate in CH$_2$Cl$_2$ in the presence of triethylamine to give ethyl α-(β,β,β-trichloroethoxycarbonylamino)-(2-hydroxythiazol-4-yl)acetate.

Analysis-Calcd. for C$_{10}$H$_{11}$O$_5$N$_2$SCl$_3$: N, 7.41; Found: N, 7.39

NMR(ppm, 100 MHz, CDCl$_3$): 1.26(3H,t,—CH$_2$C$\underline{H}_3$), 4.22(2H,q,—C$\underline{H}_2$CH$_3$), 4.70(2H,s,Cl$_3$CC$\underline{H}_2$), 5.42(1H,d, >C$\underline{H}$—COOC$_2$H$_5$), 7.24(1H,s,5-H).

EXAMPLE 24

To a solution of 1.93 g. of ethyl α-oxyimino-β-oxo-γ-chlorobutyrate in 10 ml. of ethanol is added 1.27 g. of ethylthionocarbamate and the mixture is heated for 2 hours under reflux. After cooling ethanol is evaporated then the remaining oily substance is purified by means of silica gel chromatography to give ethyl α-oxyimino-(2-hydroxythiazol-4-yl)acetate. The ester is identical with the substance obtained in Example 22 in all respects.

EXAMPLE 25

To a solution of 2.65 g. of ethyl α-acetamido-β-oxo-γ-bromobutyrate in 10 ml. of ethanol is added 1.09 g. of methylthionocarbamate. The mixture is heated for 1.5 hours under reflux and concentrated under reduced pressure. The concentrate is dissolved in chloroform. The chloroform layer is washed, dried and concentrated to give ethyl α-acetamido-(2-hydroxythiazol-4- yl)acetate as oily material. This ester (2.0 g.) is dissolved in 10 ml. of methanol and to this is added a solution of 3.09 g. of Ba(OH)$_2$.8H$_2$O in 50 ml. of water and the whole mixture is stirred at 70° C. for 3 hours. After cooling, gaseous CO$_2$ is bubbled into the reaction mixture to cause precipitation of BaCO$_3$.BaCO$_3$ thus precipitated is filtered off and the filtrate is passed through a column packed with ion-exchange resin [Amberlite IR-120(H) to give purified 2-hydroxythiazol-4-ylglycine. This substance is identical with the sample obtained in Example 21 in all respects.

EXAMPLE 26

To a solution of 2.2 g. of ethyl α-methoxyimino-β-oxo-γ-bromobutyrate in 40 ml. of ethanol are added 1.22 g. of dimethylaniline and 2.2 g. of N-(β,β,β-trichloroethoxycarbonyl)thiourea. The mixture is heated for 1.5 hours under reflux and concentrated under reduced pressure. The concentrate of the reaction mixture is recrystallized from ligroin to give ethyl α-methoxyimino-[2-(β,β,β-trichloroethoxycarbonylamino)-thiazol-4-yl]acetate as crystals. 1.84 g. Melting point: 125°–128° C.

Analysis-Calcd. for C$_{11}$H$_{12}$O$_5$N$_3$SCl$_3$: C, 32.65; H, 2.99; N, 10.38. Found: C, 32.81; H, 3.14; N, 10.19.
NMR(ppm, 100 MHz, CDCl$_3$): 7.15(1H,s,5-H).

EXAMPLE 27

To a solution of 8.1 g. of ethyl α-methoxyimino-[2-(β,β,β-trichloroethoxycarbonylamino)thiazol-4-yl]acetate in 50 ml. of ethanol is added a solution of 11.2 g. of KOH in a mixture of 30 ml. of water and 150 ml. of ethanol. The whole mixture is stirred at room temperature for 1 hour, and then concentrated under reduced pressure. The residue is extracted with ethyl acetate. The water layer is made acidic with 10% aq. HCl and the separated solid is collected. Recrystallization of the solid from aq. methanol gives α-methoxyimino-[2-(β,β,β-trichloroethoxycarbonylamino)thiazol-4-yl]acetic acid. 4.1 g. Melting point: 162°–163° C.

Analysis-Calcd. for C$_9$H$_8$O$_5$N$_3$SCl$_3$: C, 28.70; H, 2.14; N, 11.16. Found: C, 28.64; H, 2.11; N, 11.06
NMR (ppm, 100 MHz, CDCl$_3$+d$_6$-DMSO): 7.26(1H,s,5-H).

EXAMPLE 28

Ethyl α-methoxyimino-[2-(β,β,β-trichloroethoxycarbonylamino)thiazol-4-yl]acetate (2.02 g.) dissolved in 150 ml. of ethanol containing 10% HCl is hydrogenated in the presence of 2.0 g. of 5% Pd/carbon. After 240 ml. of hydrogen is absorbed, the reaction mixture is filtered and the filtrate is condensed under reduced pressure. The residue is washed with ether and suspended in 70 ml. of ethyl acetate followed by the addition of 20 ml. of 5% aq. NaHCO$_3$. The ethyl acetate layer is separated, washed, dried and condensed to give [2-(β,β,β-trichloroethoxycarbonylamino)thiazol-4-yl]glycine ethyl ester. 1.22 g.

Analysis-Calcd. for C$_{10}$H$_{12}$O$_4$N$_3$SCl$_3$: C, 31.89; H, 3.21; N, 11.16. Found: C, 31.91; H, 3.00; N, 10.63
NMR(ppm, 100 MHz, CF$_3$COOD): 5.82(1H,s, >C$\underline{H}$—COOC$_2$H$_5$), 7.74(1H,s,5-H).

EXAMPLE 29

(1) A solution of 19.3 g. of ethyl α-oxyimino-β-oxo-γ-chlorobutyrate and 8.0 g. of thiourea in 200 ml. of ethanol is heated for 2 hours under reflux. The mixture is condensed under reduced pressure and the residue is dissolved in 10% aq. HCl. The solution is washed twice with ether to remove unreacted butyrate and is adjusted to pH 7.0–7.5 with NaHCO$_3$. Chloroform extraction of the mixture gives ethyl α-oxyimino-2-aminothiazol-4-ylacetate. 6.4 g. Melting point: 137°–138° C. (dec.).

Analysis-Calcd. for C$_7$H$_9$O$_3$N$_3$S: C, 39.06; H, 4.21; N, 19.52. Found: C, 39.64; H. 4.09; N, 19.62.
IR(Nujol, cm$^{-1}$): 3430(C=NOH), 1710(ester)

(2) Ethyl α-oxyimino-2-aminothiazol-4-yl-acetate (2.15 g.) obtained in the foregoing part is dissolved in a mixture of 20 ml. of 50% aq. formic acid and 10 ml. of methanol. To this is added 1.5 g. of zinc dust and the mixture is stirred for 3 hours under ice-cooling. The filtered reaction mixture is condensed under reduced pressure and the concentrate is passed through a column packed with ionexchange resin [Amberlite IR-120(H)]. The column is washed with water to remove formic acid and then is eluted with 10% aq. ammonia to give 2-aminothiazol-4-yl-glycine. 1.49 g. Recrystallization from aq. ethanol gives pure sample; Melting point: 186°–190° C.(dec.).

Analysis-Calcd. for C$_5$H$_7$O$_2$N$_3$S.½H$_2$O: C, 32.96; H, 4.43; N, 23.06, Found: C, 32.94; H, 4.61; N, 22.22
NMR(ppm, 100 MHz, CF$_3$COOD): 5.25 (1H,s,>C$\underline{H}$—COOH), 6.75 (1H,s,5-H).
Violet color with Ninhydrin reagent.

EXAMPLE 30

A solution of 19.3 g. of thiourea and 53.5 g. of ethyl α-oxyimino-βoxo-δ-chlorobutyrate in 300 ml. of ethanol is stirred for 3 hours at room temperature, and condensed under reduced pressure. Water (200 ml.) is added to the residue and the obtained aqueous solution is washed twice with ether. To this are added 130 ml. of 85% aq. formic acid and 150 ml. of ethanol. Under ice-cooling 37 g. of zinc dust is added gradually to this mixture and stirred for 3 hours at room temperature.

The filtered reaction mixture is passed through a column packed with ion-exchange resin (Amberlite IR-120(H). The column is washed with water and eluted with 10% aq. ammonia to give purified 2-aminothiazol-4-ylglycine (27.5 g.) which is identical with the sample obtained in Example 29 in all respects.

EXAMPLE 31

Ethyl α-oxyimino-2-aminothiazol-4-ylacetate hydrochloride (503 mg.) is dissolved in 10 ml. of 50% aq. formic acid and 5 ml. of ethanol. Zinc dust (300 mg.) is added to this solution under ice-cooling and stirred for 3 hours. The reaction mixture is condensed under reduced pressure below 30° C., and the residue is made pH 7.5 by adding 1N-NaOH. Ethyl acetate extraction gives 2-aminothiazol-4-ylglycine ethyl ester. 130 mg.
NMR(ppm, 60 MHz, CF$_3$COOD): 1.04(3H,t,—CH$_2$C$\underline{H}_3$), 4.18(2H,q,—C$\underline{H}_2$CH$_3$), 5.35(1H,s,>C$\underline{H}$—COOC$_2$H$_5$), 6.90(1H,s,5-H). Mass: m/e 201,0549(theoretical: 201,0571)

EXAMPLE 32

To a solution of 26.6 g. of ethyl α-acetamido-β-oxo-γ-bromobutyrate in a mixture of 50 ml. of ethanol and 20 ml. of ether are added 9.14 g. of thiourea and 15 ml. of pyridine. The mixture is stirred for 1 hour at room temperature and then 4 hours under reflux. The reaction mixture is condensed under reduced pressure and 50 ml. of ethyl acetate is added to the residue. The mixture is extracted with 3N—HCl. The water layer thus separated is made pH 10 by adding 1N—NAOH and extracted with ethyl acetate.

The ethyl acetate extract is washed, dried and condensed. To this concentrate is added small quantity of chloroform to cause crystallization of ethyl α-acetamido-2-aminothiazol-4-ylacetate. 7.0 g. Melting point: 161.1° C.

Analysis-Calcd. for $C_9H_{13}O_3N_3S$: C, 44.43; H, 5.39; N, 17.27. Found: C, 44.46; H, 5.24; N, 16.99

EXAMPLE 33

To a solution of 34.6 g. of ethyl α-acetamido-β-oxo-γ-bromobutyrate in a mixture of 50 ml. of ethanol and 20 ml. of ether are added 18.9 g. of N-acetylthiourea and 15 ml. of pyridine. The mixture is heated under reflux for 4 hours, and condensed under reduced pressure. The condensate is extracted with ethyl acetate and the extract is washed with 5% aq. $NaHCO_3$, then with water, and dried. The oily substance which is obtained from the extract by removal of the solvent is purified by silica gel chromatography to give ethyl α-acetamido-2-acetamidothiazol-4-ylacetate. 4.46 g. Melting point: 148.9°–150° C.

Analysis-Calcd. for $C_{11}H_{15}O_4N_3S \cdot \frac{1}{4}H_2O$: C, 45.59; H, 5.39; N, 14.50. Found: C, 45.73; H, 6.40; N, 14.21

EXAMPLE 34

To a solution of 2.51 g. of N-(β,β,β-trichloroethoxycarbonyl)thiourea and 2.66 g. of ethyl α-acetamido-β-oxo-γ-bromobutyrate in 50 ml. of ethanol is added 1.8 g. of N,N-dimethylaniline. The mixture is stirred for 24 hours at room temperature, and condensed under reduced pressure. The residue is dissolved in 30 ml. chloroform and the solution is washed with 3N-HCl, water, and dried. The solid matter which is obtained by removal of chloroform is purified by silica gel chromatography to give ethyl α-acetamido-2-(β,β,β-trichloroethoxycarbonylamino)thiazol-4-ylacetate. 1.43 g. Melting point: 161.9° C.

Analysis-Calcd. for $C_{12}H_{14}O_5N_3SCl_3 \cdot \frac{1}{2}H_2O$: C, 33.70; H, 3.54; N, 9.82. Found: C, 33.69; H, 3.64; N, 10.06
NMR(ppm, 100 MHz, $d_6$-DMSO):
1.15(3H,t,—$CH_2CH_3$), 4.09(2H,q,—$CH_2CH_3$),
1.88(3H,s,$COCH_3$), 4.96(2H,s,$Cl_3CCH_2$),
5.42(1H,d,>C$\underline{H}$COO$C_2H_5$), 7.13(1H,s,5-H).

EXAMPLE 35

To a suspension of 100 mg. of ethyl α-acetamido-2-(β,β,β-trichloroethoxycarbonylamino)thiazol-4-ylacetate in 5 ml of water is added 2 ml. of 1N-NaOH and the mixture is stirred for 2 hours at room temperature. The reaction mixture is washed with ethyl acetate and the water layer is made pH 2.0 with 1N-HCl, and then extracted with ethyl acetate. The extract is washed, dried, and condensed to give N-acetyl-2-(β,β,β-trichloroethoxycarbonylamino)thiazol-4-ylglycine. 65 mg. Melting point: 158.0° C.

Analysis-Calcd. for $C_{10}H_{10}O_5N_3SCl_3 \cdot \frac{1}{2}H_2O$: C, 30.05; H, 2.77; N, 10.51. Found: C, 30.15; H, 2.52; N, 10.23.
NMR(ppm, 100 MHz, $d_6$-DMSO): 1.89(3H,s,$COCH_2$), 4.97(2H,s,$Cl_3CCH_2$), 5.40(1H,d,>C$\underline{H}$COOH), 7.10(1H,s,5-H).

EXAMPLE 36

To a solution of 238 mg. of ethyl α-oxyimino-β-oxo-γ-bromobutyrate in 10 ml. of ethanol is added 251 mg. of N-(β,β,β-trichloroethoxycarbonyl)thiourea and the mixture is heated under reflux for 6 hours. After cooling, 50 ml. of chloroform is added and the organic solution is washed with water and dried over anhydrous magnesium sulfate. Evaporation of the solvent followed by chromatographic purification on silica gel affords 164 mg. of ethyl α-oxyimino-α-[2-(β,β,β-trichloroethoxycarbonylamino)thiazol-4-yl)acetate.

Analysis-Calcd. for $C_{10}H_{10}N_3O_5SCl_3$: C, 30.74; H, 2.58; N, 10.75; Cl, 27.23. Found: C, 30.95; H, 2.51; N, 10.75; Cl, 27.02.
NMR(ppm, 100 MHz, $CDCl_3$): 1.35(3H,t,$C\underline{H_3}CH_2$), 4.36(2H,q,$CH_3C\underline{H_2}$), 4.87(2H,s,$Cl_3CC\underline{H_2}$), 7.94(1H,s,thiazole ring proton).

EXAMPLE 37

A solution of 2.0 g. of ethyl α-oxyimino-α-(2-(β,β,β-trichloroethoxycarbonylamino)thiazol-4-yl)acetate in 50 ml. of 10% HCl-ethanol is hydrogenated over 0.5 g. of 5% palladium-on charcoal under shaking. The reaction stops when 90 ml. of hydrogen is absorbed. Additional 1.5 g. of the catalyst is added and 170 ml. of hydrogen is absorbed. Insoluble material is filtered off and the filtrate is concentrated under reduced pressure. The residue is washed with ether, and separated. The separated solid is dissolved in 5 ml. of water and neutralized with 10% sodium hydrogen carbonate aq. solution, and then extracted with chloroform. The extract is washed with water, drying over anhydrous magnesium sulfate and subjected to the evaporation of the solvent. The resultant residue is followed by chromatographic purification on silica gel column to afford 560 mg. of 2-(β,β,β-trichloroethoxycarbonylamino)thiazol-4-ylglycine ethyl ester.

Analysis-Calcd. for $C_{10}H_{12}N_3O_4SCl_3$: C, 31.89; H, 3.21; N, 11.16. Found: C, 31.91; H, 3.00; N, 10.63.
NMR(ppm, 100 MHz, $CF_3CO_2D$): 1.37(3H,t,$C\underline{H_3}CH_2$), 4.47(2H,q,$C\underline{H_2}CH_3$), 4.98(2H,s,$Cl_3CCH_2$), 5.82(1H,s,$C\underline{H}$), 7.74 (1H,s,thiazole ring proton).

EXAMPLE 38

To a solution of 3.40 g. of 2-(β,β,β-trichloroethoxycarbonylamino)thiazol-4-ylglycine ethyl ester in 50 ml. of chloroform are added gradually 1.2 g. of triethylamine and 2.50 g. of β,β,β-trichloroethoxycarbonyl chloride under stirring at room temperature. After 30 minutes stirring, 100 ml. of chloroform is added to the mixture and the obtained organic solution is washed with saturated NaCl aq. solution, 1N-hydrochloric acid and then with water, and dried over anhydrous magnesium sulfate. After the evaporation of the solvent n-hexane is added to the residue to afford crude product. The crude product is recrystallized from a mixture of ligroin and n-hexane to give 4.11 g. of 2-(β,β,β-trichloroethoxycarbonylamino)thiazol-4-yl-N-(β,β,β-trichloroethoxycarbonyl)glycine ethyl ester. Yield 82%.

Analysis-Calcd. for $C_{13}H_{13}N_3O_6SCl_6$: C, 28.28; H, 2.37; N, 7.61. Found: C, 28.39; H, 2.38; N, 7.71
NMR(ppm, 100 MHz, $CDCl_3$): 1.21(3H,t,$C\underline{H_3}CH_2$), 4.60(2H,q,$CH_3C\underline{H_2}$), 4.83 and 4.86(4H,two s,$Cl_3CCH_2$), 5.60(1H,d,CH), 6.98(1H,s,thiazole ring proton), 7.38(1H,d,α-NH).

EXAMPLE 39

To a solution of 3.82 g. of 2-(β,β,β-trichloroethoxycarbonylamino)thiazol-4-yl-N-(β,β,β-trichloroethoxycarbonyl)-glycine ethyl ester in 150 ml. of ethanol is added a solution of 1.94 g. of potassium hydroxide in 10 ml. of water while stirring a room temperature. After 30 minutes stirring, the solution is concentrated under reduced pressure and 50 ml. of water is added to the residue. The aqueous solution is washed with ethyl acetate, adjusted to pH 2.0 with 1N-hydrochloric acid and extracted twice each with 70 ml. of ethyl acetate. The combined extracts are washed with water, dried over anhydrous magnesium sulfate and concentrated under reduced pressure. n-Hexane is added to the residue to separate crude material. The crude material is recrystallized from a mixture of ethyl acetate and ligroin to afford 1.83 g. of 2-(β,β,β-trichloroethoxycarbonylamino)thiazol-4-yl-N-(β,β,β-trichloroethoxycarbonyl)-glycine. Yield 50%.

NMR(ppm, 100 MHz, CDCl₃): 4.80(4H,s,Cl₃CCH₂), 4.65 (1H,s,2-NH), 5.48(1H, broad d,CH), 6.14(1H,broad d,α-NH), 6.95(1H,s thiazole ring proton).

EXAMPLE 40

To a suspension of 3.46 g. of 2-aminothiazol-4-ylglycine in 100 ml. of N,N-dimethylacetamide is added dropwise 12.66 g. of β,β,β-trichloroethoxycarbonyl chloride while stirring for 30 minutes at room temperature. After further 30 minutes stirring, 250 ml. of ethyl acetate is added to the reaction mixture and the resulting solution is washed with 70 ml. of 1N-hydrochloric acid. The ethyl acetate is separated and extracted 3 times with 50 ml. of 3% aq. potassium hydroxide solution. The combined aqueous extracts are washed with ethyl acetate, adjusted to pH 2.0 with 1N-hydrochloric acid and extracted 3 times each with 100 ml. of ethyl acetate. The combined extracts are washed with water, dried over anhydrous magnesium sulfate and concentrated under reduced pressure. n-Hexane is added to the oily residue to precipitate crude material. Crude material is separated and recrystallized from a mixture of ethyl acetate and ligroin to afford 510 mg. of 2-(β,β,β-trichloroethoxycarbonylamino)thiazol-4-yl-N-(β,β,β-trichloroethoxycarbonyl)-glycine. This product is identical with the compound in Example 39 in all respects.

EXAMPLE 41

To a suspension of 2.4 g. of 7-amino-3-(1-methyl-1H-tetrazol-5-ylthiomethyl)-3-cephem-4-carboxylic acid in 20 ml. of dimethylacetamide is added 2.4 g. of α-hydroxy-2-(β,β,β-trichloroethoxycarbonylamino)-thiazol-4-ylacetic acid cyclic carboxy anhydride (obtained by the procedure described in Example 4) and the mixture is stirred for 15 hours at room temperature. Ethyl acetate (100 ml.) is added to the reaction mixture and filtered. The filtrate is extracted several times with 5% aq. NaHCO₃. The combined extract is adjusted to pH 3.0 with 10% aq. HCl and extracted with ethyl acetate. The ethyl acetate layer is washed with saturated aq. NaCl and dried. Evaporation of the solvent gives 7β-{α-hydroxy-(2-(β,β,β-trichloroethoxycarbonylamino)thiazol-4-yl)acetamido}-3-(1-methyl-1H-tetrazol-5-ylthiomethyl)-3-cephem-4-carboxylic acid (1.8 g.) as a jelly which is then dissolved in 100 ml. of 90% aq. formic acid under ice cooling. To this solution is added 1.8 g. of zinc dust and stirred for 1 hour under ice-cooling. The reaction mixture is filtered and condensed under reduced pressure. Water (100 ml.) is added to the condensate and H₂S gas is bubbled into the aqueous solution to precipitate zinc sulfide. Zinc sulfide is filtered off and the filtrate is condensed under reduced pressure and the concentrate is dissolved in 5% aq. NaHCO₃ solution and the solution is passed through a column packed with polystyrene resin (Amberlite XAD-2) to give purified 7β-(α-hydroxy-α-(2-aminothiazol-4-yl)acetamido)-3-(1-methyl-1H-tetrazol-5-ylthiomethyl)-3-cephem-4-carboxylic acid sodium salt. Analysis-Calcd. for $C_{15}H_{15}O_5N_8S_3Na\cdot 3H_2O$: C, 32.14; H, 3.78; N, 19.99. Found: C, 32.53; H, 3.77; N, 19.50. NMR(ppm, 100 MHz, D₂O): 3.71(2H,q,2-CH₂), 4.14(3H,s,N-CH₃), 5.28(1H,s,>CH—CONH), 5.22(1H,d,6-H), 5.75(1H,d,7-H), 6.84(1H,s,5-H).

EXAMPLE 42

To a solution of 100.8 mg. of NaHCO₃ and 127.6 mg. of 5-mercapto-1-methyl-1H-tetrazole in 10 ml. of water is added 486 mg. of sodium 7β-(α-hydroxy-(2-aminothiazol-4-yl)acetamido)cephalosporanate. The mixture is stirred at 55° C. for 20 hours. After cooling the mixture is passed through a column packed with polystyrene resin (Amberlite XAD-2) to give purified sodium 7β-(α-hydroxy-(2-aminothiazol-4-yl)-acetamido)-3-(1-methyl-1H-tetrazol-5-ylthiomethyl)-3-cephem-4-carboxylate, which is identical with the sample obtained in Example 41 in all respects.

EXAMPLE 43

To a suspension of 781 mg. of α-ethoxyimino-(2-(β,β,β-trichloroethoxycarbonylamino)thiazol-4-yl)acetic acid in 15 ml. of CH₂Cl₂ is added 625 mg. of phosphorus pentachloride. The mixture is homogenized by stirring for 10 seconds. After stirring at room temperature for 1 hour, the solvent is removed under reduced pressure and the residue is dissolved in 10 ml. of acetone. On the other hand 7-amino-3-(1-methyl-1H-tetrazol-5-ylthiomethyl)-3-cephem-4-carboxylic acid (657 mg.) and NaHCO₃ (1.68 g.) are dissolved in a mixture of 20 ml. of water and 10 ml. of acetone. To this solution while ice-cooling, the foregoing acetone solution is added dropwise in a period of 30 minutes. After the dropping, the mixture is stirred at room temperature for 2 hours, and condensed under reduced pressure to remove acetone. The concentrate is washed with ethyl acetate, adjusted to pH 2.0 with 1N-HCl and extracted with ethylacetate. The ethyl acetate extract is washed with water, dried over anhydrous magnesium sulfate and condensed to give 7β-{α-ethoxyimino-(2-(β,β,β-trichloroethoxycarbonylamino)thiazol-4-yl)acetamido}-3-(1-methyl-1H-tetrazol-5-ylthiomethyl)-3-cephem-4-carboxylic acid. 925 mg. Yield 660%.

NMR(ppm, 100 MHz CF₃COOD): 1.50(3H,t,CH₂CH₃), 4.60(2H,q,—CH₂CH₃), 3.85(2H,q,2-CH₂), 4.12(3H s,N-CH₃), 4.98 (2H,s,Cl₃CCH₂—), 5.38(1H d,6-H), 6.02(1H,q,7-H), 7.91(1H,s,5-H).

EXAMPLE 44

Sodium 7β-{α-ethoxyimino-(2-(β,β,β-trichloroethoxycarbonylamino)thiazol-4-yl)acetamido} cephalosporanate (667 mg.) NaHCO₃ (90 mg.) and 5-mercapto-1-methyl-1H-tetrazole (120 mg.) are dissolved to 20 ml. of water. The mixture is stirred at 60° C. for 8 hours and filtered. The filtrate is adjusted to pH 2.0 with 1N-HCl and the solid is separated. The separated solid is filtered, washed with water and dried over phosphorus pentachloride under reduced pressure to give 7β-{α-ethoxyimino-(2-(β,β,β-trichloroethoxycarbonylamino)-thiazol-4-yl)acetamido}-3-(1-methyl-1H-tetrazol-5-ylthiomethyl)-3-cephem-4-carboxylic acid. (238 mg.) which is identical with the sample obtained in Example 43 in all respects.

EXAMPLE 45

To a suspension of 2.92 g of α-ethoxyimino-(2-(chloroacetamido)thiazol-4-yl)acetic acid in 50 ml of methylene chloride is added 2.08 g of phosphorus pentachloride. The mixture is stirred for 2 hours at room temperature, after which time methylene chloride is distilled off and the redisue is dissolved in 30 ml of acetone. The acetone solution is added dropwise under ice-cooling in a period of 15 minutes, to the solution of 3.29 g of 7-amino-3-(1-methyl-1H-tetrazol-5-ylthiomethyl)-3-cephem-4-carboxylic acid and 8.4 g of sodium bicarbonate dissolved in a mixture of 100 ml of water and 50 ml of acetone. After the addition has been completed, the obtained solution is stirred at room temperature for 2 hours and concentrated under reduced pressure to remove acetone. The concentrate is washed with ethyl acetate and adjusted to pH 2.0 with 3N hydrochloric acid under ice-cooling, followed by extracting with ethyl acetate. The ethyl acetate layer is washed with water and dried over anhydrous magnesium sulfate, followed by distillation of the solvent to give 3.80 g of 7β- α-ethoxyimino-[2-(chloroacetamido)thiazol-4-yl]acetamido}-3-(1-methyl-1H-tetrazol-5-ylthiomethyl)-3-cephem-4-carboxylic acid. Yield 63.1%.

NMR(ppm, 60 MHz, d$_6$-DMSO): 1.34(3H,t,C$\underline{H_3}$CH$_2$—), 3.56(2H,broad S,2-CH$_2$), 3.95(3H,S,$\overline{N}$-CH$_3$), 4.05-4.50(4H,m,CH$_3$C$\underline{H_2}$— and 3-CH$_2$), 4.24(2H,S,ClC$\underline{H_2}$CO), 5.04(1H,d,6-H), 5.70(1H,d,7-H), 7.82(1H,S,thiazole ring proton).

IR(KBr,cm$^{-1}$): 1760(β-lactam), 1035(=N—O—C).

EXAMPLE 46

To a solution of 3.90 g of sodium 7β-{α-ethoxyimino-[2-(chloroacetamido)thiazol-4-yl]acetamido}-3-(1-methyl-1H-tetrazol-5-ylthiomethyl)-3-cephem-4-carboxylate in 50 ml of water is added 1.52 g of thiourea. The mixture is stirred at room temperature for 3 hours and adjusted to pH 2.0 with 1N hydrochloric acid. The resulting precipitates are filtered, washed with water and dried to obtain 2.40 g of 7β-[α-ethoxyimino-(2-aminothiazol-4-yl)acetamido]-3-(1-methyl-1H-tetrazol-5-ylthiomethyl)-3-cephem-4-carboxylic acid. Yield 73.1%.

NMR(ppm, 60 MHz,d$_6$-DMSO): 1.26(3H,t,CH$_3$CH$_2$—), 3.84(3H,S,N—CH$_3$), 3.90–4.40(4H,m,CH$_3$C$\underline{H_2}$— and 3—CH$_2$), 5.02(1H,d,6-H), 5.70(1$\overline{H}$,d,7-H), 7.94(1H,S,thiazole ring proton).

IR(KBr,cm$^{-1}$): 1770 β-lactam), 1030(=N—O—C).

EXAMPLE 47

2.0 g of 7β-[α-ethoxyimino-(2-aminothiazol-4-yl)-acetamido]-3-(1-methyl-1H-tetrazol-5-ylthiomethyl)-3-cephem-4-carboxylic acid is dissolved in 50 ml of 90% formic acid. To the solution is added 2.48 g of zinc dust under stirring and cooling at the temperature of $-10°$ C., and the mixture is further stirred for 15 minutes. After the reaction has been completed, the insoluble materials are filtered off. Into the filtrate is poured ether to precipitate white solid, which is centrifugally separated and washed three times with ether and dried (yield; 1.66 g). This white solid is dissolved in aq. solution of sodium bicarbonate. The solution is subjected to the purification using a column of Amberlite XAD-2 and the fractions eluted with water are lyophilized to obtain sodium 7β-[(2-aminothiazol-4-yl)glycylamido]-3-(1-methyl-1H-tetrazol-5-ylthiomethyl)-3-cephem-4-carboxylate.

NMR(ppm, 100MHz,D$_2$O): 3.94(3H,S,N-CH$_3$), 6.74(1H,S,thiazole ring proton).

IR(KBr,cm$^{-1}$): 1760(β-lactam).

UV(H$_2$O, nm): 260(cephem)

EXAMPLE 48

(1) To a suspension of 6.25 g of phosphorus pentachloride in 45 ml of anhydrous methylene chloride cooled at $-10°$ C., is added 20 ml of anhydrous methylene chloride solution containing 2.4 g of pyridine and the mixed solution is stirred for 30 minutes. To the solution is dropwise added a solution of 9.3 g of 7β-(2-thienylacetamido)-3-(1-methyl-1H-tetrazol-5-ylthiomethyl)-3-cephem-4-carboxylic acid benzhydryl ester in 30 ml of anhydrous methylene chloride during 30 minutes under stirring and keeping at $-20°$ C.--$10°$ C. The mixture is further stirred for 2 hours at the same temperature and then cooled to $-30°$ C.--$20°$ C., followed by adding dropwise 56 ml of methanol. Thus obtained solution is stirred for 30 minutes, keeping the temperature of the solution between $-5°$ C. and $5°$ C., and 60 ml of water is added dropwise thereto, followed by further stirring for 30 minutes. Methylene chloride layer is washed with saturated aq. NaCl solution and concentrated. To the concentrate is added a mixture of water and ethyl acetate under stirring to give 4.746 g of 7-amino-3-(1-methyl-1H-tetrazol-5-ylthiomethyl)-3-cephem-4-carboxylic acid benzhydryl ester as a crystal Yield 64.0%.

(2) To a suspension of 2.05 g of α-ethoxyimino-α-[2-(chloroacetamido)thiazol-4-yl]acetic acid in 50 ml of methylene chloride is added 1.50 g of phosphorus pentachloride under cooling. The mixture is stirred for 2 hours at room temperature and subjected to the distillation of methylene chloride. The residue is dissolved in 20 ml of tetrahydrofuran. The tetrahydrofuran solution is dropwise added while stirring to a solution of 2.92 g of 7-amino-3-(1-methyl-1H-tetrazol-5-ylthiomethyl)-3-cephem-4-carboxylic acid benzhydryl ester dissolved in 50 ml of absolute methylene chloride, followed by the addition of 2.87 g of pyridine under ice-cooling. After the addition has been completed and the temperature of the reaction solution becomes the same as the room temperature, the solution is stirred for 2 hours and then concentrated. The residue is dissolved in a mixture of 100 ml of ethyl acetate and a little amount of tetrahydrofuran. Thus obtained solution is washed with dilute hydrochloric acid, sodium bicarbonate aq. solution and water in this order, dried over anhydrous magnesium sulfate and concentrated. The concentrate is purified by means of a column of silica gel. The fractions eluted with the mixture of ethyl acetate and chloroform (1:1) are concentrated to obtain 2.36 g of 7β-{α-ethoxyimino[2-(chloroacetamido)thiazol-4-yl)acetamido}-3-(1-methyl-1H-tetrazol-5-ylthiomethyl)-3-cephem-4-carboxylic acid benzhydryl ester. Yield 50%.

NMR(ppm, 60MHz, CDCl$_3$): 1.34(3H,t,C$\underline{H_3}$CH$_2$-), 3.68(2H, broad S,2-CH$_2$), 3.80(3H,S,$\overline{N}$-CH$_3$), 4.26(2H,S,ClC$\underline{H_2}$CO), 5.04(1H,d,6-H), 5.92(1H,q,7-H), 6.94(1$\overline{H,S}$,-C$\underline{H}$Ph$_2$), 7.20–7.60(10H,m,Ph$_2$), 7.90(1H,S, thiazole ring proton), 8.45(1H,d,7-NH).

EXAMPLE 49

To a solution of 2.2 g of 7β-{α-ethoxyimino-[2-(chloroacetamido)thiazol-4-yl]acetamido-}-3-(1-methyl-1H-tetrazol-5-ylthiomethyl)-3-cephem-4-carboxylic acid benzhydryl ester in 20 ml of tetrahydrofuran is added a solution of 550 mg of thiourea in 20 ml of ethanol, followed by addition of 50 mg of triethylbenzylammonium bromide. The mixture is stirred for 20 hours at room temperature and concentrated. The residue is dissolved in a mixture of ethyl acetate and tetrahydrofuran and the solution was washed with aq. sodium bicarbonate solution and then water, followed by drying over anhydrous magnesium sulfate. The dried solution is subjected to distillation of the solvent to give powder which is washed with chloroform and ether and dried. The procedure yields 1.047 g of 7$\beta$-[$\alpha$-ethoxyimino-(2-aminothiazol-4-yl)acetamido]-3-(1-methyl-1H-tetrazol-5-ylthiomethyl)-cephem-4-carboxylic acid benzhydryl ester. Yield 52.9%.

NMR(ppm, 60MHz, CDCl$_3$+d$_6$-DMSO(3:1)): 1.38(3H,t, CH$_3$CH$_2$-), 3.78(2H, broad S, 2-CH$_2$), 3.90(3H,S,N-$\overline{\text{CH}}_3$), 4.30(2H, broad S, 3-CH$_2$), 4.38(2H,q,CH$_3$C$\underline{\text{H}}_2$), 5.14(1H,d,6H), 6.00(1H,d,7-H), 6.88(1H,S,C$\underline{\text{H}}$Ph$_2$), 7.20–7.60(10H,m,Ph$_2$), 7.48(1H,S,thiazole ring proton).

EXAMPLE 50

To a solution of 750 mg of 7$\beta$-[$\alpha$-ethoxyimino-(2-aminothiazol-4-yl)acetamido]-3-(1-methyl-1H-tetrazol-5-ylthiomethyl)-3-cephem-4-carboxylic acid benzhydryl ester in 10 ml of 90% formic acid is added 654 mg of zinc dust, cooling to $-10°$ C. After the mixture is stirred for 20 minutes at $-10°$ C. and further for 10 minutes at room temperature, the insoluble materials is filtered off. The filtrate is neutralized with aq. sodium bicarbonate solution and extracted with ethyl acetate. The ethyl acetate layer is washed with water and dried over anhydrous magnesium sulfate, after which time the solvent is distilled off to give 465 mg of foamy materials. All of the foamy materials are dissolved in a mixture of 2 ml of trifluoroacetic acid and 0.5 ml of anisole, stirred for 30 minutes under ice-cooling and then for 5 minutes at room temperature. Thus obtained solution is concentrated, and to the residue is poured ether to precipitate a solid. The solid is washed twice with ether and dried to obtain 320 mg of solid product. This solid product is dissolved in an excess amount of aq. sodium bicarbonate solution and purified with a column of Amberlite XAD-2. The fractions eluted with water is lyophilized to obtain sodium 7$\beta$-[(2-aminothiazol-4-yl)-glycylamido]-3-(1-methyl-1H-tetrazol-5-ylthiomethyl)-3-cephem-4-carboxylate. This product is identical with the compound obtained in Example 47 in all respects.

EXAMPLE 51

To a solution of 18.7 g of ethyl $\alpha$-ethoxyimino-$\beta$-oxobutyrate in 100 ml of chloroform gradually is dropwise added a solution of 15.9 g of bromine in 20 ml of chloroform under ice-cooling. The solution is stirred for 30 minutes at the same temperature and further 1.5 hours at room temperature. The reaction mixture is washed with water, aq. sodium bicarbonate solution and then water is this order, followed by drying over anhydrous magnesium sulfate. The dried solution is subjected to the evaporation of the solvent, and to the residue is added 250 ml of ethanol and 15.2 g of thiourea. Thus mixture is refluxed for 2 hours and cooled, followed by the distillation of the solvent under reduced pressure. To the residue is added 250 ml of water to precipitate a solid which is collected by means of filtration and washed with water and dried. The procedure gives 17.9 g of ethyl $\alpha$-ethoxyimino-2-aminothiazol-4-ylacetate hydrobromide. Yield 55%.

Analysis-Calcd. for C$_9$H$_{14}$N$_3$O$_3$SBr: C, 33.34; H, 4.35; N, 12.96 Found C, 32.52; H, 3.98; N, 12.92.

NMR(ppm, 100MHz, d$_6$-DMSO): 130 and 1.32 (6H,two t, C$\underline{\text{H}}_3$CH$_2$), 4.28 and 4.37(4H, two q, CH$_3$C$\underline{\text{H}}_2$), 7.63(1H,S, thiazole ring proton), 9.12(2H, broad S, NH$_2$)

EXAMPLE 52

To a solution of 2.43 g of ethyl $\alpha$-ethoxyimino-2-aminothiazol-4-ylacetate hydrobromide in 25 ml of anhydrous N,N-dimethylacetamide is added 1.43 g of chloroacetyl chloride under cooling and stirring. The solution is stirred for 30 minutes under ice-cooling and then for 30 minutes at room temperature. To the reaction mixture is added 150 ml of ethyl acetate and the mixture is repeatedly washed with saturated aq. NaCl solution. The ethyl acetate layer is dried over anhydrous magnesium sulfate, and subjected to the distillation of the solvent under reduced pressure. To the residue is added water to precipitate solid material. The solid is collected by filtration and dried. The procedure gives 1.90 g of ethyl $\alpha$-ethoxyimino-2-(chloroacetamino)thiazol-4-ylacetate. Yield 79%.

NMR(ppm, 100MHz, d$_6$-DMSO): 1.24 and 1.27 (6H, two t, C$\underline{\text{H}}_3$CH$_2$), 4.22(4H, two q, CH$_3$C$\underline{\text{H}}_2$), 4.30(2H,S,Cl$\overline{\text{CH}}_2$CO), 7.99 (1H,S, thiazole ring proton).

EXAMPLE 53

1.06 g of ethyl $\alpha$-ethoxyimino-2-(chloroacetylamino)-thiazol-4-ylacetate is suspended in a solution of 0.94 g of potassium hydroxide in a mixture of 40 ml of ethanol and 2 ml of water and the suspension is stirred at room temperature to make it to be a solution, followed by further stirring for 45 minutes at room temperature. The reaction solution is subjected to the distillation of ethanol under reduced pressure and the residue is adjusted to pH 2.0 with 1 N hydrochloric acid under ice-cooling, to precipitate crystals. The crystals are filtered, washed with water and dried. The procedure yields 0.88 g of $\alpha$-ethoxyimino-2-(chloroacetylamino)thiazol-4-ylacetic acid. Yield 91%.

Analysis-Calcd. for C$_9$H$_{10}$N$_3$O$_4$SCl: C, 37.05; H, 3.45; N, 14.41. Found: C, 37.17; H, 3.44; N, 14.09

NMR(ppm, 100MHz, d$_6$-DMSO): 1.28(3H,t,C$\underline{\text{H}}_3$CH$_2$), 4.22(2H,q, CH$_3$C$\underline{\text{H}}_2$), 4.32(2H,S,ClC$\overline{\text{H}}_2$CO), 8.00(1H,S,thiazole ring proton).

EXAMPLE 54

(1) To a solution of 5.03 g of N-($\beta,\beta,\beta$-trichloroethoxycarbonyl)thiourea and 5.32 g of ethyl $\alpha$-ethoxyimino-$\beta$-oxo-$\gamma$-briomobutyrate in 50 ml of ethanol is added 3.03 g of N,N-dimethylaniline and the mixture is heated for 2 hours in water bath of 80° C. The reaction solution is subjected to the distillation of ethanol and the residue is dissolved in ethyl acetate. The ethyl acetate solution is washed with dilute hydrochloric acid and then water, and dried, followed by the distillation of the solvent to give 7.85 g of ethyl $\alpha$-(2-$\beta,\beta,\beta$-trichloroethoxycarbonylaminothiazol-4-yl)-$\alpha$-ethoxyiminoacetate as an oil.

(2) To a solution of 2.00 g of ethyl $\alpha$-(2-$\beta,\beta,\beta$-trichloroethoxycarbonylaminothiazol-4-yl)-$\alpha$-ethoxyiminoacetate in 40 ml of methanol is added 20 ml of 1 N sodium hydroxide. The solution is stirred for 2 hours at 50° C. and concentrated. To the concentrate is added 50 ml of water and thus obtained solution is washed twice with ethyl acetate. Aqueous layer is adjusted to pH 2.0 with 3 N hydrochloric acid to separate white solid. The white solid is filtered, washed with water and dried to give 1.40 g of α-ethoxyimino-2-(β,β,β-trichloroethoxycarbonylamino)thiazol-4-ylacetic acid. Yield 74.9%.
Analysis-Calcd. for $C_{10}H_{10}N_3O_5SCl_3$: C, 30.75; H, 2.58; N, 10.76 Found C, 30.87; H, 2.41; N, 10.66
NMR(ppm, 60MHz, d$_6$—DMSO): 1.13(3H,t,$CH_3$CH$_2$), 4.06(2H,q, CH$_3$$CH_2$), 4.90(2H,S,Cl$_3$C$CH_2$O), 7.40(1H,S,thiazole ring proton).

EXAMPLE 55

To a suspension of 6.0 g of 7α-methoxy-7β-amino-3-desacetoxycephalosporanic acid t-butyl ester in 180 ml of N,N-dimethylacetamide is added under stirring 8.25 g of powdered 2-(β,β,β-trichloroethoxycarbonylamino)thiazol-4-yl-α-hydroxyacetic acid cyclic carboxyanhydride and then further stirred for one hour. The reaction mixture is shaken well with 500 ml of ethyl acetate and the organic layer is washed with water, 5% sodium bicarbonate aq. solution and saturated aq. NaCl solution in this order, followed by drying over anhydrous magnesium sulfate. The ethyl acetate layer is subjected to the distillation of ethyl acetate to give 10.2 g of crude 7α-methoxy-7α-[2-(β,β,β-trichloroethoxycarbonylamino)thiazol-4-yl-α-hydroxyacetamido]-3-desacetoxycephalosporanic acid t-butyl ester as an oil. To a solution of this oily product in 400 ml of 90% formic acid is added 10 g of zinc dust under cooling and stirring and the mixture is reacted for 2 hours. After insoluble materials are filtered off, the filtrate is added to 200 ml of saturated NaCl aq. solution, and the resultant solution is extracted with ethyl acetate. The ethyl acetate layer is washed with water and dried, followed by the distillation of ethyl acetate to obtain 5.3 g of crude 7α-methoxy-7β-[(2-aminothiazol-4-yl)-α-hydroxyacetamido]-3-desacetoxycephalosporanic acid t-butyl ester as an oil.
This oily product is added to a mixture of 25 ml of trifluoroacetic acid and 25 ml of anisole under ice-cooling, and the mixture is stirred for 30 minutes under the same condition. To the reaction mixture is poured 200 ml of absolute ether, and resulting precipitates are collected by means of filtration. The precipitates are dissolved in 30 ml of 5% sodium bicarbonate aq. solution, and thus obtained solution is passed through a column of Amberlite XAD-2, followed by elution with water. The procedure yields 525 mg. of sodium 7α-methoxy-7β-[(2-aminothiazol-4-yl)-α-hydroxyacetamido]-3-desacetoxycephalosporanate as a powder.
Analysis-Calcd. for $C_{14}H_{15}O_6N_4S_2Na \cdot 2H_2O$: C, 36.67; H, 4.17; N, 12.22 Found C, 36.23; H, 4.38; N, 11.97
NMR(ppm, 100MHz, CF$_3$COOD): 2.15(3H,S,3-CH$_3$), 3.45(3H,S, 7-OCH$_3$), 6.25(1H,S,thiazole ring proton).

EXAMPLE 56

To a solution of 27.3 g of ethyl α-methoxyimino-β-oxobutyrate in 120 ml of chloroform is dropwise added a solution of 25.3 g of bromine in 30 ml of chloroform over a period of 30 minutes. The solution is stirred for 1 hour at room temperature, and washed with dilute sodium bicarbonate aq. solution and water and dried. The dried solution is subjected to the distillation of the solvent to give an oily crude product of ethyl α-methoxyimino-β-oxo-γ-bromobutyrate. The crude product is dissolved in 250 ml of ethanol and 24 g of thiourea is added thereto, followed by refluxing for 3 hours. After cooling, the precipitates are collected by filtration, washed with ethanol and then suspended in 300 ml of a mixture of ethyl acetate and tetrahydrofuran (1:1). To the suspension is added to 200 ml of 10% sodium bicarbonate aq. solution and the mixture is thoroughly shaken. The organic layer is dried and subjected to the distillation of the solvent to give crystal, followed by washing with ether. The procedure gives 16.86 g of ethyl α-methoxyimino-α-(2-aminothiazol-4-yl)acetate. Melting point: 112°–113° C.
Analysis-Calcd. for $C_8H_{11}N_3O_3S$: C, 41.91; H, 4.84 Found: C, 41.20; H, 4.70 NMR(ppm, 60MHz, CDCl$_3$): 4.04(3H,S, OCH$_3$), 7.44(1H,S, thiazole ring proton).

EXAMPLE 57

To a solution of 10 g of ethyl α-methoxyimino-α-(2-aminothiazol-4-yl)acetate in 100 ml of dimethylacetamide is dropwise added 5.91 g of chloroacetyl chloride under ice-cooling. After the stirring for 1 hour at room temperature, the reaction mixture is poured into ice-water and the resultant solution is extracted with ethyl acetate. The organic layer is washed and dried, followed by the distillation of solvent to give 12.66 g of ethyl α-methoxyimino-α-[2(chloroacetamido)thiazol-4-yl]acetate as a crystal. Melting point: 81°–82° C.
Analysis-Calcd. for $C_{10}H_{12}N_3O_4SCl$: C, 39.29; H, 3.96 Found: C, 38.74; H, 3.58
NMR(ppm, 60MHz, CDCl$_3$): 4.10(3H,S,OCH$_3$), 4.24(2H,S,Cl$CH_2$CO—) 7.94(1H,S,thiazole ring proton).

EXAMPLE 58

12.66 g of ethyl α-methoxyimino-α-[2-(chloroacetamido)-thiazol-4-yl]acetate is added to a solution of 11.74 g of potassium hydroxide in a mixture of 25 ml of water and 500 ml of ethanol. After stirring for 20 minutes at room temperature, the reaction solution is subjected to the distillation of ethanol under reduced pressure. The residue is added to water, and the resultant solution is made acidic with addition of N-hydrochloric acid, followed by separating the insoluble materials by filtration. The procedure yields 10.54 g of α-methoxyimino-α-[2-(chloroacetamido)thiazol-4-yl]acetic acid. Melting point: 182°–183° C.
Analysis-Calcd. for $C_8H_8N_3O_4SCl$: C, 34.60; H, 2.90; N, 15.13 Found: C, 34.53; H, 3.00; N, 14.80
NMR(ppm, 60MHz, d$_6$-DMSO): 4.00(3H,S,OCH$_3$), 4.38(2H,S, Cl$CH_2$CO), 8.00(1H,S, thiazole ring proton).

EXAMPLE 59

To a suspension of 555.4 mg of α-methoxyimino-α-[2-(chloroacetamido)thiazol-4-yl]acetic acid in 5 ml of methylene chloride is added 416.3 mg of phosphorus pentachloride under ice-cooling. The resultant solution is stirred for 30 minutes, and n-hexane is added thereto to precipitate 620 mg of α-methoxyimino-α-[2-(chloroacetamido)-thiazol-4-yl]acetyl chloride hydrochloric acid salt.
Analysis-Calcd. for $C_8H_7N_3O_3SCl_2 \cdot HCl$: C, 28.89; H, 2.42; N, 12.63 Found: C, 28.35; H, 2.81; N, 12.00
5.26 g of the above-mentioned salt is added under ice-cooling to a solution of 2.66 g of pyridine and 4 g of 7-aminocephalosporanic acid t-butyl ester in 60 ml of methylene chloride. After the stirring for 1 hour at room temperature, 60 ml of chloroform is added to the reaction mixture and the resultant solution is washed twice with 0.5 N hydrochloric acid and then with water. After drying, the solution is subjected to the distillation to obtain 5 g of white powder of 7β-{α-methoxyimino-α-[2-(chloroacetamido)thiazol-4-yl]acetamido}-cephalosporanic acid t-butyl ester. Melting point: 126°–127° C.

Analysis-Calcd. for $C_{22}H_{26}N_5O_8S_3Cl$: C, 44.93; H, 4.46; N, 11.91 Found: C, 44.74; H, 4.64; N, 11.61

NMR(ppm, 60 MHz, $CDCl_3$): 1.50(9H,S, t-$C_4H_9$), 2.10(3H,S, $CH_3CO$), 4.10(3H,S,$OCH_3$), 4.28(2H,S,$ClCH_2CO$), 7.84 (1H,S, thiazole ring proton).

EXAMPLE 60

5 of 7β-{α-methoxyimino-α-[2-(chloroacetamido)-thiazol-4-yl]acetamido}cephalosporanic acid t-butyl ester obtained in Example 59, 970.5 mg of thiourea and 250 mg. of triethylbenzylammonium bromide are dissolved in a mixture of 25 ml of ethanol and 500 ml of tetrahydrofuran. The solution is stirred at room temperature through a night. The reaction mixture is poured into 100 ml of 10% sodium bicarbonate aq. solution and extracted with ethyl acetate. The ethyl acetate layer is separated and concentrated. The oily concentrate is subjected to column chromatography packed with silica gel to obtain 2.23 g of 7β-[α-methoxyimino-α-(2-aminothiazol-4-yl)acetamido]cephalosporanic acid t-butyl ester as a powder.

NMR(ppm, 60 MHz, $CDCl_3$): 1.54(9H,S,t-$C_4H_9$), 2.08(3H,S,$CH_3CO$), 4.12(3H,S,$OCH_3$), 7.45(1H,S,thiazole ring proton).

This powder is dissolved in a mixture of 1.6 ml of anisole and 16 ml of trifluoroacetic acid and the solution is stirred for 2 hours at room temperature, followed by the addition of 200 ml of a mixture of ether and hexane (10:1) to precipitate 7β-[α-methoxyimino-α-(2-aminothiazol-4-yl)-acetamido]cephalosporanic acid trifluoroacetic acid salt which is collected by filtration and washed with ether. Yield 1.45 g.

NMR(ppm, 60 MHz, $CF_3COOH$): 1.85(3H,S,$CH_3CO$), 4.00(3H,S,$OCH_3$), 7.74(1H,s,thiazole ring proton).

EXAMPLE 61

A solution of 450 mg of 7β-[α-methoxyimino-α-(2-aminothiazol-4-yl)acetamido]cephalosporanic acid trifluoroacetic acid salt and 170 mg of sodium bicarbonate in 5 ml of water is passed through a column of Amberlite XAD-2 and eluted with water. The procedure yields 141 mg of sodium 7β-[α-methoxyimino-α-(2-aminothiazol-4-yl)acetamido]-cephalosporanate. Melting point: 162°–163° C.(dec.).

Analysis-Calcd. for $C_{16}H_{16}N_5O_7S_2Na.2H_2O$: C, 37.43; H, 3.93; N, 13.64 Found: C, 37.10; H, 4.13; N, 13.34

NMR(ppm, 100 MHz, $D_2O$): 2.17(3H,S, $CH_3CO$), 4.13(3H,S, $OCH_3$), 7.58(1H,S,thiazole ring proton).

EXAMPLE 62

7β-[α-methoxyimino-α-(2-aminothiazol-4-yl)acetamido]cephalosporanic acid trifluoroacetic acid salt is dissolved in a solution of 272 mg of 1-methyl-5-mercapto-1H-tetrazole, 555 mg. of sodium bicarbonate and 68 mg of triethylbenzylammonium bromide in 10 ml of water. The solution is heated at 60° C. in nitrogen atmosphere for 6 hours. After cooling, the reaction solution is passed through a column of Amberlite XAD-2 and eluted with water and then with 2.5% ethanol. The procedure yields sodium 7β-[α-methoxyimino-α-(2-aminothiazol-4-yl)acetamodo]-3-(1-methyl-1H-tetrazol-5-ylthiomethyl)-3-cephem-4-carboxylate. Melting point: 174°–175° C.(dec.).

Analysis-Calcd. for $C_{16}H_{16}N_9O_5S_3Na.2H_2O$: C, 33.74; H, 3.54; N, 22.13 Found: C, 34.25; H, 3.81; N, 21.69

NMR(ppm, 100 MHz, $D_2O$): 4,10(3H,S,N-$CH_3$), 4.14(3H,S,$OCH_3$), 7.58(1H,S,thiazole ring proton).

The above-mentioned procedure gives a small amount of sodium 7β-[α-methoxyimino-α-(2-aminothiazol-4-yl)-acetamodo]-3-desacetylcephalosporanate as a by-product.

Melting point: 195°–196° C.(dec.).

Analysis-Calcd. for $C_{14}H_{14}N_5O_6S_2Na.3H_2O$: C, 34.35; H, 4.11; N, 14.30 Found: C, 34.43; H, 4.13; N, 13.14

NMR(ppm, 60 MHz, $D_2O$): 4.04(3H,S, $OCH_3$), 7.46(1H,S,thiazole ring proton), 3.52(2H,q,2-$CH_2$).

EXAMPLE 63

To a suspension of 3.4 g of 7-amino-3-(1-methyl-1H-tetrazol-5-ylthiomethyl)-3-cephem-4-carboxylic acid in 25 ml of dimethylacetamide is added 2.0 g of α-methoxyimino-α-[2-(chloroacetamido)thiazol-4-yl]acetyl chloride hydrochloric acid salt under stirring. After the further stirring for 12 hours at room temperature, the reaction mixture is poured into water and extracted with ethyl acetate. The ethyl acetate extract is washed with water and dried and subjected to the distillation of the solvent. To the residue is added ethyl acetate and insoluble materials are filtered off. The filtrate is contentrated under reduced pressure to obtain crude product 1.114 g of 7β-{α-methoxyimino-α-[2-(chloroacetamido)thiazol-4-yl]acetamido}-3-(1-methyl-1H-tetrazol-5-ylthiomethyl)-3-cephem-4-carboxylic acid as an oil. The oily product is dissolved in 20 ml of a mixture of ethanol and tetrahydrofuran (1:1) and to the solution is added 430 mg of thiourea, followed by stirring for 15 hours at room temperature. The reaction solution is concentrated to dryness under reduced pressure and to the residue is added 10 ml of water, followed by stirring to precipitate insoluble materials. The insoluble materials is collected by filtration and dissolved in 10% sodium bicarbonate aq. solution. The solution is passed through a column of Amberlite XAD-2, and eluted with water and then with 2.5 ethanol to obtain sodium 7β-[α-methoxyimino-α-(2-aminothiazol-4-yl)acetamido]-3-(1-methyl-1H-tetrazol-5-ylthiomethyl)-3-cephem-4-carboxylate. This product is identical with the compound obtained in Example 62 in all respects.

EXAMPLE 64

A solution of 10.45 g of α-ethoxyimino-α-[2-(trichloroethoxycarbonylamino)thiazol-4-yl]acetic acid ethyl ester in a mixture of 10% hydrochloric acid and ethanol is catalytic-hydrogenated over 8.0 g of 5% palladium on charcoal at room temperature under atomospheric pressure. After the absorption of two equivalents of hydrogen, the catalyst in the reaction mixture is filtered off and the filtrate is concentrated to dryness under reduced pressure. By the procedure, 7.43 g of α-amino-α-[2-(trichloroethoxycarbonylamino)-thiazol-4-yl]acetic acid ethyl ester hydrochloric acid salt is obtained (yield, 72%). This product is suspended in ethyl acetate and the obtained suspension is washed with saturated sodium bicarbonate aq. solution, washed with water and dried over anhydrous magnesium sulfate. The oily product obtained by the distillation of the solvent, is dissolved in 60 ml of N,N-dimethylformamide and, to the solution is added 4.2 g of tetramethylguanidine and then 3.94 g of t-butyloxycarbonylazide, followed by the stirring for 15 hours at room temperature. The reaction mixture is poured into water and extracted with ethyl acetate. The organic layer is washed with 1 N hydrochloric acid and then saturated NaCl aq. solution and dried over anhydrous magnesium sulfate. The oily product obtained by the distillation of the solvent is purified by a column chromatography packed with silica gel. The procedure gives 4.06 g of α-t-butyloxycarbonylamino-α-[2-(trichloroethoxycarbonylamino)thiazol-4-yl]acetic acid ethyl ester (yield, 46.5%). Melting point: 94°–95° C.

Analysis-Calcd. for $C_{15}H_{20}N_3H_{20}N_3O_6SCl_3$: C, 37.79; H, 4.23; N, 8.81 Found: C, 37.64; H, 4.28; N, 8.73

EXAMPLE 65

To a solution of 2.80 g of α-t-butyloxycarbonylamino-α-[2-(trichloroethoxycarbonylamino)-thiazol-4-yl]acetic acid ethyl ester in 60 ml of 90% formic acid is added 2.80 g of zinc dust under cooling and stirring. The mixture is stirred for 1 hour and zinc dust is filtered off. The filtrate is poured into water and the resultant solution is extracted with ethyl acetate. The organic layer is washed with saturated sodium bicarbonate aq. solution and then water, and dried over anhydrous magnesium sulfate. The distillation of the solvent gives 1.26 g (yield, 71.2%) of α-t-butyloxycarbonylamino-α-(2-aminothiazol-4-yl)acetic acid ethyl ester as crystals. Melting point: 143°–144° C.

Analysis-Calcd. for $C_{12}H_{19}N_3O_4S$: C, 47.83; H, 6.35; N, 13.95 Found: C, 47.79; H, 6.27; N, 13.70

EXAMPLE 66

To a solution of 1.26 g of α-t-butyloxycarbonylamino-α-(2-aminothiazol-4-yl)acetic acid ethyl ester in 5 ml of N,N-dimethylacetamide is added 708 mg of chloroacetyl chloride under stirring. After the stirring for further 1 hour at room temperature, the reaction solution is poured into water and extracted with ethyl acetate. The organic layer is washed with saturated sodium bicarbonate aq. solution and then water and dried over anhydrous magnesium sulfate. The distillation of the solvent gives 1.435 g of α-t-butyloxycarbonylamino-α-[2-(chloroacetamido)thiazol-4-yl]acetic acid ethyl ester as crystals (yield, 90.8%). Melting point: 192°–193° C.

Analysis-Calcd. for $C_{14}H_{20}ClN_3O_5S$: C, 44.50; H, 5.35; N, 11.12 Found: C, 44.87, H, 5.55; N, 10.94

EXAMPLE 67

To a solution of 920 mg of α-t-butyloxycarbonylamino-α-[2-(chloroacetamido)thiazol-4-yl]acetic acid ethyl ester in 20 ml of ethanol is added 1.4 ml of aqueous solution containing 681 mg of potassium hydroxide and the mixture is stirred for 15 minutes at room temperature. The reaction solution is concentrated to dryness under reduced pressure and the residue is dissolved in water. The aqueous solution is adjusted to pH 2.0 with 1 N hydrochloric acid and extracted with ethyl acetate. The organic layer is washed with water and dried over anhydrous magnesium sulfate. The solvent is distilled to obtain 690 mg of α-t-butyloxycarbonylamino-α-[2-(chloroacetamino)thiazol-4-yl]acetic acid as crystals (yields, 81%). Melting point: 169°–170° C.(dec.).

Analysis:Calcd. for $C_{12}H_{16}ClN_3O_5S$: C, 41.21; H, 4.61; N, 12.01 Found: C, 41.40; H, 4.68; H, 11.74

EXAMPLE 68

To a suspension of 349 mg of α-t-butyloxycarbonylamino-α-[2-(chloroacetamido)thiazol-4-yl ]acetic acid in 5 ml of methylene chloride is added 249 mg of phosphorous pentachloride, and the mixture is stirred at room temperature. The mixture is added dropwise under stirring to the solution of 494 mg of 7β-amino-3-(1-methyl-1H-tetrazol-5-ylthiomethyl)-3-cephem-4-carboxylic acid diphenylmethyl ester dissolved in 5 ml of methylene chloride, followed by the addition of 474 mg of pyridine. After that, the stirring is continued for further 1 hour at room temperature. The reaction solution is washed with 0.5 N hydrochloric acid and then with wafer, and dried. The oily product obtained by the distillation of the solvent is purified by a column chromatography packed with silica gel. The procedure gives 513 mg of 7β-{α-t-butyloxycarbonylamino-α-[2-(chloroacetamido)thiazol-4-yl)acetamido}-3-(1-methyl-1H-tetrazol-5-ylthiomethyl)-3-cephem-4-carboxylic acid diphenylmethyl ester.

To a solution of 407 mg of this product in 40 ml of a mixture of tetrahydrofuran and ethanol (1:1) is added 152 mg of thiourea, and the mixture is stirred for 15 hours at room temperature. The reaction solution is condensed under reduced pressure and the presidue is dissolved in ethyl acetate. The ethyl acetate solution is washed with water and then dried. The oily product obtained by the distillation of the solvent is dissolved in 5 ml of a mixture of trifluoroacetic acid and anisole (10:1), and the solution is stirred for 2 hours at room temperature, followed by pouring into 50 ml of ether to precipitate a crystalline product. The crystalline product is collected by filtration to give 7β-[(2-aminothiazol-4-yl)glycylamido]-3-(1-methyl-1H-tetrazol-5-ylthiomethyl)-3-cephem-4-carboxylic acid trifluoroacetic acid salt. This product is dissolved in 5% sodium bicarbonate aq. solution and the solution is passed through a column of Amberlite XAD-2, followed by the elution with water. The procedure gives 103 mg of sodium 7β-[(2-aminothiazol-4-yl)glycylamido]-3-(1-methyl-1H-tetrazol-5-ylthiomethyl)-3-cephem-4-carboxylate. This product is identical with the compound obtained in Example 47 in all respects.

EXAMPLE 69

To a solution of 11 g of 2-aminothiazol-4-ylglycine ethyl ester in 100 ml of dimethylacetamide is added dropwise 17 g of chloroacetyl chloride for 40 minutes under ice-cooling and the mixture is stirred at room temperature over a night. To the reaction mixture is added 200 ml of ice-water and the mixture is extracted with ethyl acetate. The organic layer is washed with water, dried and concentrated to obtain 14.8 g of 2-chloroacetamidothiazol-4-yl N-chloroacetylglycine ethyl ester as colorless crystals. Melting point: 102.5°–103.5° C.

NMR(ppm, 60 MHz, CDCl₃): 4.16(2H,S,ClCH₂CO), 4.32(2H,S,ClCH₂CO),

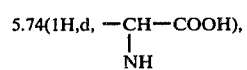

7.14(1H,S,thiazole ring proton).

EXAMPLE 70

To a solution of 3.54 g of 2-chloroacetamidothiazol-4-yl N-chloroacetylglycine ethyl ester in 30 ml of ethanol is added dropwise a solution of 1.68 g of potassium hydroxide in 15 ml of water under ice-cooling, followed by the stirring for 15 minutes. Ethanol is distilled under reduced pressure and the residue is made acidic with 10% hydrochloric acid, followed by the extraction with ethyl acetate. The ethyl acetate layer is washed with water and dried. The distillation of ethyl acetate gives 2.38 g of 2-chloroacetamidothiazol-4-yl N-chloroacetylglycine as colorless crystals. Melting point: 184°–186° C.

NMR(ppm, 60 MHz, $d_6$-DMSO): 4.36(2H,S,ClCH$_2$CO), 4.58(2H,S,ClCH$_2$CO),

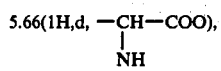

5.66(1H,d, —CH—COO),
            |
           NH 7.40(1H,S,thiazole ring proton).

EXAMPLE 71

To a suspension of 752 mg of 2-chloroacetamidothioazol-4-yl N-chloroacetylglycine in 10 ml of methylene chloride is added 499 mg of phosphorous pentachloride. The mixture is homogenized under stirring at room temperature. The homogenized mixture is added to a suspension of 600 mg of 7β-amino-3-(1-methyl-1H-tetrazol-5-ylthiomethyl)-3-cephem-4-carboxylic acid suspended in 10 ml of dimethylacetamide and the resultant mixture is stirred for 5 hours at room temperature. The reaction mixture is poured into icewater and the mixture is made acidic with 10% hydrochloric acid, followed by the extraction with ethyl acetate. After washed with water and dried, the extract is subjected to distillation to give crude product of 7β-[(2-chloroacetamidothiazol-4-yl)-N-chloroacetylglycylamido]-3-(1-methyl-1H-tetrazol-5-ylthiomethyl)-3-cephem-4-carboxylic acid as an oil. The crude product is dissolved in 100 ml of ethanol and to the solution is added 456 mg of thiourea, followed by stirring for 15 hours at room temperature. Ethanol is distilled off under reduced pressure and the residue is dissolved in 5% sodium bicarbonate aq. solution, which is passed through a column of Amberlite XAD-2, followed by elution with water to obtain 113 mg of sodium 7β-[(2-aminothiazol-4-yl)glycylamido]-3-(1-methyl-1H-tetrazol-5-ylthiomethyl)-3-cephem-4-carboxylic acid. This product is identical with the compound obtained in Example 47 in all respects.

What we claims is:

1. A compound of the formula:

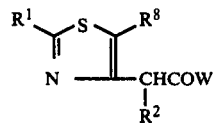

wherein $R^1$ represents amino, protected amino, hydroxyl or protected hydroxyl, $R^2$ represents amino, protected amino, hydroxyl, protected hydroxyl or the group

represents a group of the formula

wherein $R^5$ is hydroxy or lower alkoxy, $R^8$ represents hydrogen or a halogen and W represents hydroxyl, $C_{1-4}$ alkoxyl, halogen, or OM wherein M is an alkali metal.

2. A compound of the formula:

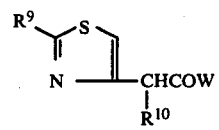

wherein each of $R^9$ and $R^{10}$ represents amino or hydroxyl, and W represents hydroxyl, $C_{1-4}$ alkoxyl, halogen, or OM wherein M is an alkali metal.

3. A compound of the formula:

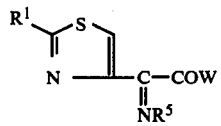

wherein $R^1$ represents amino, protected amino, hydroxyl or protected hydroxyl, $R^5$ represents hydroxyl or protected hydroxyl, and W represents hydroxyl, $C_{1-4}$ alkoxyl, halogen, or OM wherein M is an alkali metal.

4. A compound as claimed in claim 1, which is ethyl α-acetamido-α-[2-(β,β,β-trichloroethoxycarbonylamino)thiazol-4-yl]acetate.

5. A compound as claimed in claim 1, which is 2-chloroacetamidothiazol-4-yl N-chloroacetylglycine.

6. A compound as claimed in claim 1 which is α-methoxyimino-α-[2-(β,β,β-trichloroethoxycarbonylamino)thiazol-4-yl ]acetic acid.

7. A compound as claimed in claim 1 which is ethyl α-methoxyimino-α-(2-aminothiazol-4-yl)acetate.

8. A compound as claimed in claim 1 which is ethyl α-methoxyimino-α-(2-chloroacetamidothiazol-4-yl)acetate.

9. A compound as claimed in claim 1 which is α-methoxyimino-α-(2-chloroacetamidothiazol-4-yl)acetic acid.

10. A compound as claimed in claim 1 which is α-methoxyimino-α-(2-chloroacetamidothiazol-4-yl)acetyl chloride.

11. A compound as claimed in claim 3 wherein the compound is in the form of anti-isomer.

12. A compound as claimed in claim 3 wherein the compound is in the form of syn-isomer.

* * * * *

UNITED STATES PATENT AND TRADEMARK OFFICE
CERTIFICATE OF CORRECTION

PATENT NO. : 4,203,899
DATED : May 20, 1980
INVENTOR(S) : MICHIHIKO OCHIAI, TAIITI OKADA, OSAMI AKI, AKIRA MORIMOTO, KENJI KAWAKITA and YOSHIHIRO MATSUSHITA It is certified that error appears in the above-identified patent and that said Letters Patent are hereby corrected as shown below:

On the cover page of the patent, the left hand column, following "[22] Filed: April 17, 1978" insert the following:

--[30] Foreign Application Priority Data:

December 19, 1974 (JP) Japan ...146567/1974
    June 9, 1975 (GB) Great Britain...24611/1975   --

Signed and Sealed this

Twenty-first Day of April 1981

[SEAL]

Attest:

RENE D. TEGTMEYER

Attesting Officer    Acting Commissioner of Patents and Trademarks